US006872864B2

(12) United States Patent
Gajda et al.

(10) Patent No.: US 6,872,864 B2
(45) Date of Patent: Mar. 29, 2005

(54) METHOD OF CONTROLLING MONOALKYL AROMATIC PROCESS

(75) Inventors: Gregory J. Gajda, Mount Prospect, IL (US); James F. McGehee, Milan (IT)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/287,873

(22) Filed: Nov. 4, 2002

(65) Prior Publication Data

US 2003/0149320 A1 Aug. 7, 2003

Related U.S. Application Data

(63) Continuation of application No. 09/537,050, filed on Mar. 28, 2000, now Pat. No. 6,479,721, which is a continuation-in-part of application No. 09/089,563, filed on Jun. 3, 1998, now Pat. No. 6,043,402.
(60) Provisional application No. 60/049,648, filed on Jun. 16, 1997.

(51) Int. Cl.[7] .................................................. C07C 2/58
(52) U.S. Cl. ........................................ 585/467; 585/446
(58) Field of Search ................................ 585/467, 446

(56) References Cited

U.S. PATENT DOCUMENTS

| 2,403,785 | A | 7/1946 | Britton et al. | 260/671 |
|---|---|---|---|---|
| 2,592,589 | A | 4/1952 | Nickels | 260/671 |
| 4,008,290 | A | 2/1977 | Ward | 260/672 T |

(Continued)

FOREIGN PATENT DOCUMENTS

| CN | 1128249 A | 8/1996 | |
|---|---|---|---|
| DE | 550494 | 4/1932 | |
| DE | 19516717 | 11/1996 | |
| EP | 0 733 608 A1 | 9/1996 | C07C/6/12 |
| EP | 0 742 190 A1 | 11/1996 | |
| WO | WO 02/26671 A1 | 4/2002 | C07C/15/02 |

OTHER PUBLICATIONS

Document Bibliography and Abstract for CN1128249A downloaded from esp@cenet.com on Apr. 29, 2004 (1 page).
Notification of the First Office Action for Chinese Patent Application No. 99103153.9 dated Jan. 9, 2004—Chinese version (4 pages).
M.F. Bentham et al. *Development and Commercialization of Solid Acid Catalysts* DGMK conference on "Catalysis of Solid Acids and Basis" Mar. 14–15, 1996; Berlin, Germany pp. 155–166 (DGMK German Society for Petroleum and Coal Science and Technology) DGMK—Tagungsbericht 9601, ISBN 3-931850-00-5, 1996.
Bellussi, G. et al., "*Liquid–Phase Alkylation of Benzene with Light Olefins Catalyzed by $_\beta$Zeolites*" Journal of Catalysis 157 Academic Press, Inc. 1995 pp. 227–234.
Venuto, P.B. et al., "*Organic Reaction Catalyzed by Crystalline Aluminosilicates*" Journal of Catalysis 5, (1966) pp. 484–493.
Maerz, Brian et al., "*EBMax$^{SM}$: Leading Edge Ethylbenzene Technology from Mobil/Badger*" presented to the 21$^{st}$ Annual 1996 DeWitt Petrochemical Review; JW Marriot Hotel; Houston. TX, Mar. 19–21, 1996.
Ercan, C. et al., "*Mass–Transfer Effects in Liquid–Phase Alkylation of Benzene with Zeolite Catalysts*" Ind. Eng. Chem. Res. 1998, vol. 37, No. 5, pp. 1724–1728.

*Primary Examiner*—Thuan Dinh Dang
(74) *Attorney, Agent, or Firm*—John T. Tolomei; James C. Paschall; Michael A. Moore

(57) ABSTRACT

A process for the alkylation of aromatics with olefins using a solid catalyst is disclosed, wherein the olefin ratio and/or the maximum olefin concentration in the alkylation catalyst bed is maintained less than an upper limit. Such operation can decrease the catalyst deactivation rate and the formation of diphenylalkanes. This invention is applicable to processes for the production of a wide variety of commercially important alkylated aromatics, including ethylbenzene and cumene.

14 Claims, 5 Drawing Sheets

U.S. PATENT DOCUMENTS

| | | | |
|---|---|---|---|
| 4,051,191 A | 9/1977 | Ward | 260/671 R |
| 4,083,886 A | 4/1978 | Michalko | 260/672 T |
| 4,107,224 A | 8/1978 | Dwyer | 260/671 R |
| 4,169,111 A | 9/1979 | Wight | 585/323 |
| 4,587,370 A | 5/1986 | DeGraff | 585/450 |
| 4,695,665 A | 9/1987 | DeGraff | 585/450 |
| 4,870,222 A | 9/1989 | Bakas et al. | 585/323 |
| 4,876,408 A | 10/1989 | Ratcliffe et al. | 585/467 |
| 4,891,458 A | 1/1990 | Innes et al. | 585/323 |
| 4,922,053 A | 5/1990 | Waguespack et al. | 585/449 |
| 5,003,119 A | 3/1991 | Sardina et al. | 585/323 |
| 5,030,786 A | 7/1991 | Shamshoum et al. | 585/467 |
| 5,157,158 A * | 10/1992 | Berna Tejero et al. | 568/628 |
| 5,177,285 A | 1/1993 | Van Opdorp et al. | 585/467 |
| 5,227,558 A | 7/1993 | Shamshoum et al. | 585/446 |
| 5,336,821 A | 8/1994 | DeGraff et al. | 585/402 |
| 5,522,984 A | 6/1996 | Gajda et al. | 208/120 |
| 5,723,710 A | 3/1998 | Gajda et al. | 585/467 |
| 5,877,370 A | 3/1999 | Gajda | 585/467 |
| 5,902,917 A | 5/1999 | Collins et al. | 585/323 |
| 5,998,684 A | 12/1999 | Ho et al. | 585/323 |
| 6,096,935 A | 8/2000 | Schulz et al. | 585/323 |
| 6,150,578 A | 11/2000 | Ho et al. | 585/323 |
| 6,232,515 B1 | 5/2001 | Schulz et al. | 585/323 |
| 6,281,399 B1 | 8/2001 | Schulz et al. | 585/323 |

\* cited by examiner

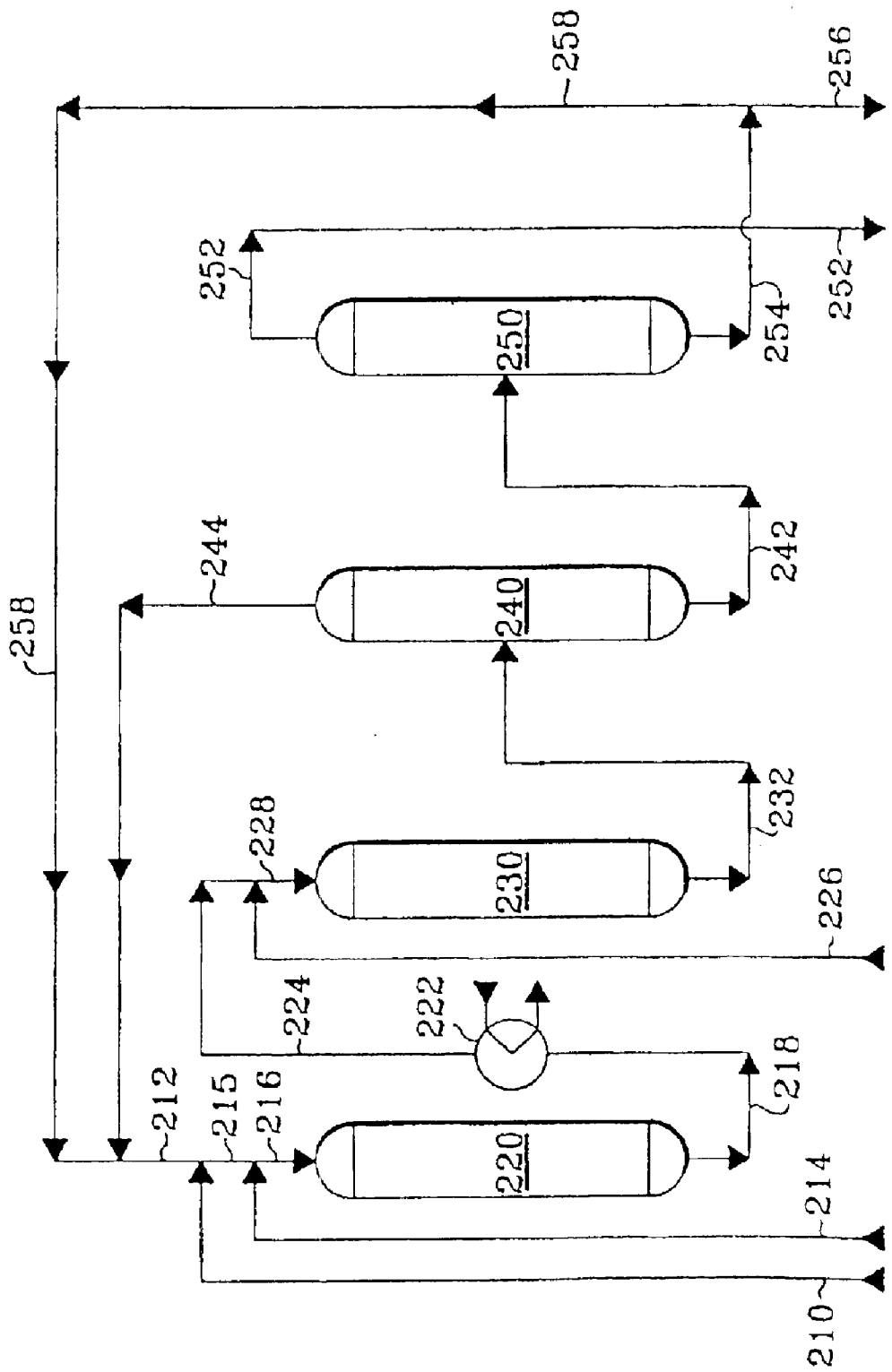

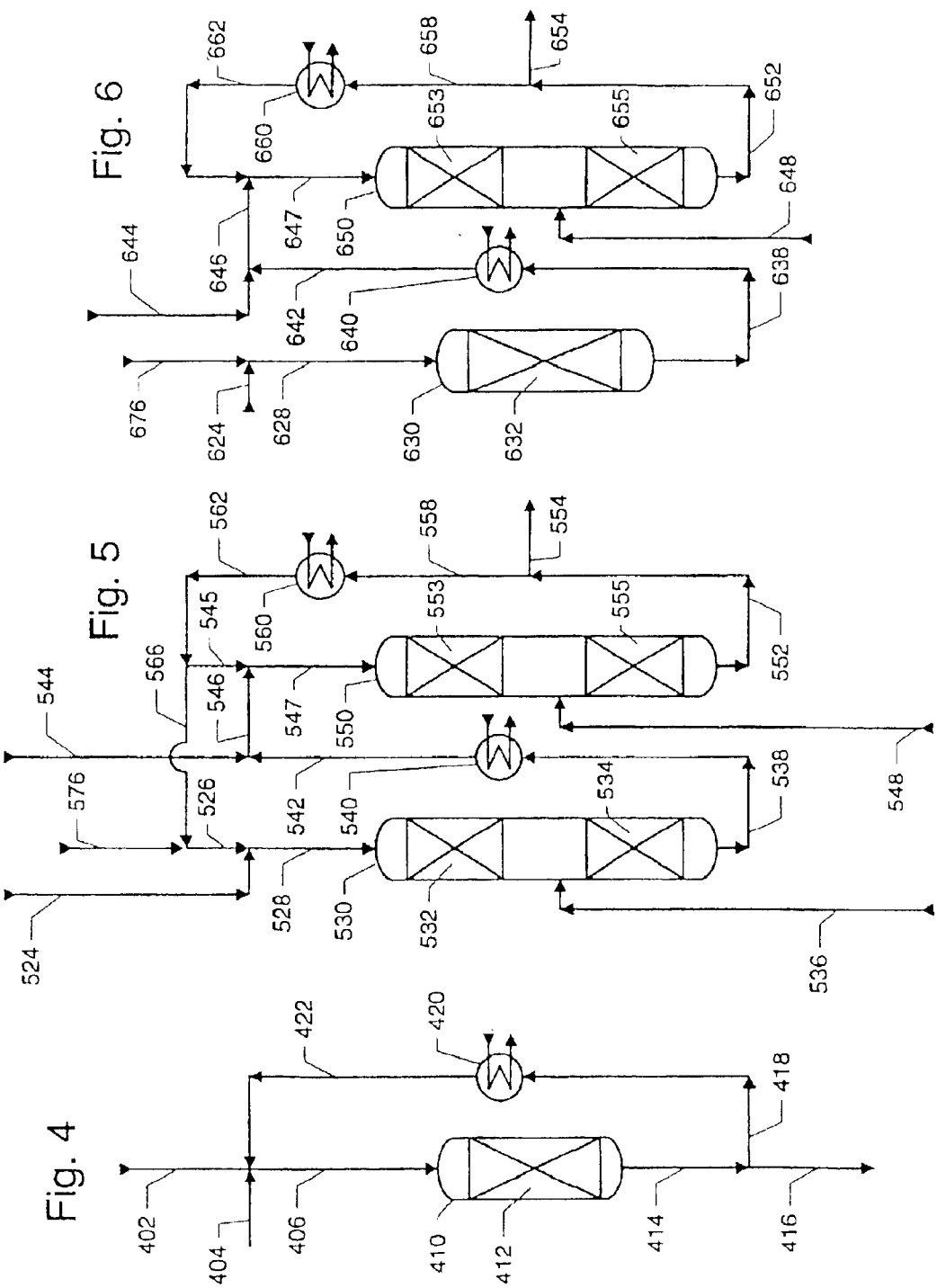

METHOD OF CONTROLLING MONOALKYL AROMATIC PROCESS

CROSS-REFERENCE TO RELATED APPLICATIONS

This application is a continuation of U.S. Application No. 09/537,050, filed Mar. 28, 2000 and issued as U.S. Pat. No. 6,479,721, which is hereby incorporated herein in its entirety and which is a continuation-in-part of U.S. application Ser. No. 09/089,563, filed June 3, 1998 and issued as U.S. Pat. No. 6,043,402, which is hereby incorporated herein in its entirety and which claims the benefit of U.S. Provisional Application No. 60/049,648, filed Jun. 16, 1997, which is hereby incorporated herein in its entirety.

FIELD OF THE INVENTION

This invention relates to a process for producing monoalkyl aromatic compounds by alkylation. Specifically, this invention relates to highly-selective alkylation and transalkylation to produce cumene and ethylbenzene.

BACKGROUND OF THE INVENTION

Alkylation of aromatic compounds with a $C_2$ to $C_4$ olefin and transalkylation of polyalkylaromatic compounds are two common reactions for producing monoalkyl aromatic compounds. Examples of these two reactions that are practiced industrially to produce ethylbenzene are the alkylation of benzene with ethylene and the transalkylation of benzene and a diethylbenzene. A simplified summary of the alkylation reaction and its common product and by-products is given below:

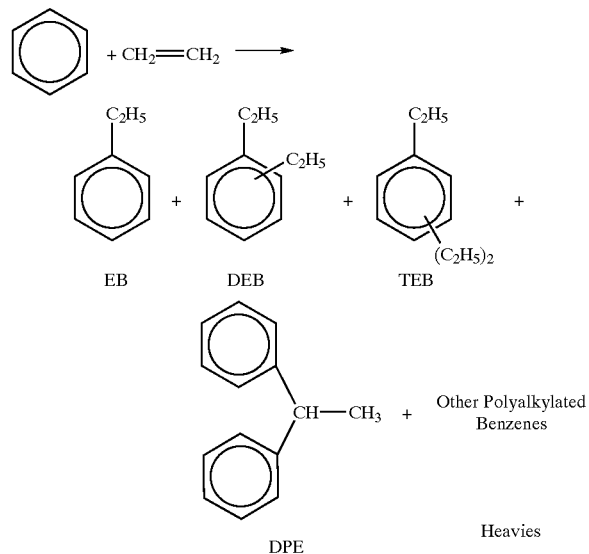

Although the formation of the diethylbenzene and triethylbenzene isomers might, at first glance, be viewed as by-products that represent a reduction in the efficient utilization of ethylene, in fact each can be readily transalkylated by benzene to produce ethylbenzene, as shown below:

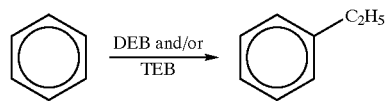

Combining alkylation and transalkylation can thus maximize ethylbenzene production. Such a combination can be carried out in a process having two reaction zones, one for alkylation and the other for transalkylation, or in a process having a single reaction zone in which alkylation and transalkylation both occur. In many cases, a single reaction zone is preferred over two reaction zones because of the savings in capital investment.

One disadvantage of alkylation-transalkylation processes, regardless of whether the alkylation and transalkylation reactions occur in the same or separate reaction zones, is that by-product 1,1-diphenylethane (1,1-DPE) can not be converted to ethylbenzene by alkylation or transalkylation, and thus 1,1-DPE represents a reduction in ethylene utilization efficiency and a loss of ethylene. In fact, the by-production of 1,1-DPE, as well as of the heavier polyethylated benzenes other than diethylbenzene and triethylbenzene, represents virtually all of the reduction in the ethylene utilization efficiency and a loss of benzene as well. As used herein, the term "heavies" refers to polyalkyl aromatics other than dialkyl and trialkyl aromatics and to other even heavier alkylation and transalkylation by-products including diphenylalkanes (DPA) and alkylated diphenylalkanes (DPAs), such as diphenylethane (DPE), alkylated diphenylethanes (DPEs), diphenylpropane (DPP), and alkylated diphenylpropanes (DPPs). The current minimum requirement for combination processes is that 1,1-DPE be not more than 1.0 wt-% relative to ethylbenzene. The formation of 1,1-DPE is assuming added importance and significance in view of the expectation in some areas of near-term minimum standards for the content of 1,1-DPE of not more than 0.5 wt-%.

In reaction zones where alkylation and transalkylation occur, it is known that the formation of 1,1-DPE depends in part on two key operating variables. The first operating variable is the molar ratio of phenyl groups per ethyl group, which is often referred to herein as the phenyl/ethyl ratio. The numerator of this ratio is the number of moles of phenyl groups passing through the reaction zone during a specified period of time. The number of moles of phenyl groups is the sum of all phenyl groups, regardless of the compound in which the phenyl group happens to be. In the context of ethylbenzene production, for example, one mole of benzene, one mole of ethylbenzene, and one mole of diethylbenzene each contribute one mole of phenyl group to the sum of phenyl groups. The denominator of this ratio is the number of moles of ethyl groups passing through the reaction zone during the same specified period of time. The number of moles of ethyl groups is the sum of all ethyl and ethenyl groups, regardless of the compound in which the ethyl or ethenyl group happens to be, except that paraffins are not included. Paraffins, such as ethane, propane, n-butane, isobutane, pentanes, and higher paraffins are excluded from the computation of the number of moles of ethyl groups. For example, one mole of ethylene and one mole of ethylbenzene each contribute one mole of ethyl group to the sum of ethyl groups, whereas one mole of diethylbenzene contributes two moles of ethyl groups and one mole of triethylbenzene contributes three moles of ethyl groups.

The second operating variable that affects the 1,1-DPE formation is the concentration of ethylene in the alkylation zone. A practical, mathematical approximation is that the concentration of ethylene depends on the molar ratio of phenyl groups per ethyl group according to the formula:

$$[\text{ethylene}] \propto [\text{phenyl/ethyl ratio}]^{-1}.$$

Thus, increasing the phenyl/ethyl ratio decreases the concentration of ethylene.

It is known that a low concentration of ethylene or a high molar ratio of phenyl groups per ethyl group minimizes formation of 1,1-DPE. The amount of 1,1-DPE formed depends on the phenyl/ethyl ratio according to the formula:

$$[1,1\text{-DPE}] \propto [\text{phenyl/ethyl ratio}]^{-2}.$$

Thus, increasing the phenyl/ethyl ratio decreases the amount of 1,1-DPE formed. Although the decrease in 1,1-DPE formation that is conferred by a small increase in phenyl/ethyl ratio may be small, it also is very significant, resulting in a high phenyl/ethyl ratio being the condition of choice for minimizing 1,1-DPE formation. However, a high phenyl/ethyl ratio increases capital and operating costs that are usually associated with the recovery of excess benzene. These costs give impetus to a search for an ethylbenzene process that minimizes 1,1-DPE formation at a low phenyl/ethyl ratio.

In the prior art, the search for a commercially-viable alkylation process that not only produces a small amount of 1,1-DPE but also operates at a low phenyl/ethyl ratio in the alkylation zone has not been fruitful. All of the prior art processes follow the same, well-known approach of dividing the reaction zone into more and more catalyst beds and injecting smaller and smaller portions of the total ethylene into each bed. Where the allowed concentration of 1,1-DPE is relatively high, this approach undoubtedly confers some benefits. For example, if benzene is alkylated with ethylene in a single-bed alkylation zone that operates at a phenyl/ethyl molar ratio of 5, then the highest concentration of ethylene, which occurs at the point of ethylene injection, is 16.7 mol-%. Downstream of the ethylene injection point, the ethylene concentration decreases to very low concentrations as ethylene is consumed and ethylbenzene is formed, while the phenyl/ethyl ratio remains essentially the same. However, if the single bed is divided into four beds in series and if one-fourth of the required ethylene is injected into each bed, then the phenyl/ethyl ratio is 20 in the first bed, 10 in the second bed, 6.7 in the third bed, and 5 in the fourth bed. Accordingly, the highest concentration of ethylene is 4.8 mol-% in the first bed, 4.5 mol-% in the second bed, 4.3 mol-% in the third bed, and 4.2 mol-% in the fourth bed. Thus, dividing the bed and splitting the ethylene injection increases the phenyl/ethyl ratio and decreases the highest ethylene concentration.

But, in order to operate at the low phenyl/ethyl ratios and to also attain the low concentrations of 1,1-DPE that are expected to become the minimum standard in the near future, this prior art approach is not viable. For example, if benzene is alkylated with ethylene in a four-bed alkylation zone that operates at an overall phenyl/ethyl molar ratio of 2 rather than 5 as in the previous example, then the phenyl/ethyl ratio ranges from 8 in the first bed to 2 in the fourth bed, and the highest ethylene concentration ranges from 11.1 mol-% in the first bed to 8.3 mol-% in the fourth bed. Compared to the previous example, the ethylene concentration in each bed approximately doubled, which would result in an unacceptable amount of 1,1-DPE formation. In order to reduce the ethylene concentrations to those in the previous example, the number of beds would have to be increased from 4 to 10, simply as a consequence of the fact that the overall phenyl/ethyl ratio had decreased from 5 to 2.

While U.S. Pat. No. 5,877,370 (Gajda) describes that a reduction in the amount of 1,1-DPE formed in the production of ethylbenzene by alkylation of benzene with ethylene can be effected by alkylating at a low concentration of ethylene, the lowest concentration of ethylene that U.S. Pat. No. 5,877,370 teaches is 1.88 wt-% (Example 6, Table 1). The highest ratio of weight of recycle effluent per weight of fresh benzene that U.S. Pat. No. 5,877,370 teaches is 3 (Example 10, Table 3) which, at a phenyl/ethyl molar ratio of 5.0, corresponds to a ratio of weight of recycle effluent per weight of fresh feed (i.e., fresh benzene and fresh olefin) of 2.5.

Thus, in response to industry's demands for lower phenyl/ethyl ratios and the market's demand for lower ethylene concentrations, the prior art process inexorably divides the reaction zone into a large number of very small catalyst beds. Because of a variety of technical, economic, and practical considerations, this inefficient solution by the prior art processes is unacceptable in the hydrocarbon processing industry.

SUMMARY OF THE INVENTION

A method has been discovered to significantly reduce the formation of diphenylalkanes and/or to significantly decrease the catalyst deactivation rate in the production of alkyl aromatics such as ethylbenzene and cumene by alkylation using solid catalysts such as zeolite beta. This invention is particularly useful at a low molar ratio of phenyl groups per alkyl group (e.g., phenyl/ethyl ratio or phenyl/propyl ratio). This invention passes an aromatic feed stream and an olefinic feed stream to an alkylation catalyst bed, where the ratio of the weight of the olefin entering the alkylation catalyst bed in the olefinic feed stream per unit time to the sum of the weights of compounds entering the alkylation catalyst bed per the same unit time, multiplied by 100, is less than 1.88. This invention uses a dilute ratio of olefin entering the alkylation catalyst bed and/or a dilute concentration of olefin in the alkylation catalyst bed to decrease the diphenylalkane formation and/or to decrease the catalyst deactivation rate. This dilution can be achieved by recycling a portion of the effluent from an alkylation reaction zone. This result using a solid catalyst such as zeolite beta was surprising and was not predictable from the prior art, which teaches that, in the production of ethylbenzene, for example, 1,1-DPE formation can be reduced only by increasing the phenyl/ethyl ratio or by increasing the number of catalyst beds. Moreover, prior art processes using Y zeolite produce more 1,1-DPE and deactivate more rapidly as a result of using the same components and streams that confer benefits when using solid alkylation catalysts such as zeolite beta. Thus, a process of alkylating benzene with ethylene at a low ethylene concentration shows a significant selectivity advantage over one operating at a high ethylene concentration. By using this invention, ethylbenzene processes can now minimize 1,1-DPE formation and/or catalyst deactivation even when operating at low molar ratios of phenyl groups per ethyl group. With the problems of 1,1-DPE formation and/or catalyst deactivation now solved by this invention, ethylbenzene processes can now operate more profitably at a low molar ratio of phenyl groups per ethyl group.

Without limiting this invention to any particular theory, two working hypotheses may describe the underlying chemistry responsible for the observed results. One hypothesis is that in the alkylation of an aromatic by an olefin, when the concentration of an olefin decreases, there is a selective decrease in the reaction between the olefin and the alkyl aromatic. The products of this reaction are an alkenyl aromatic and a paraffin that correspond to the olefin. The alkenyl aromatic can in turn serve as an active alkylating agent and react with the aromatic to form by-product diarylalkane. Applying this hypothesis to the alkylation of benzene with ethylene, the apparently anomalous formation of 1,1-DPE would result from the following reaction:

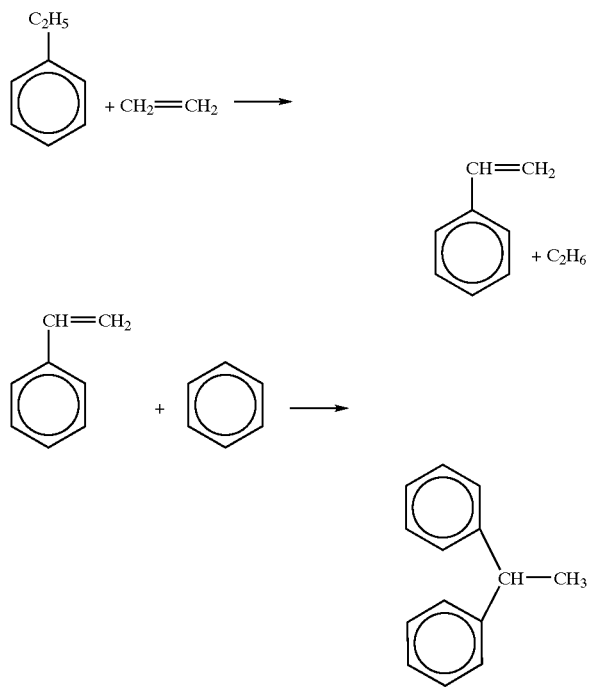

Where a catalyst is used, it is believed that the ethylbenzene and the styrene are chemisorbed on the catalyst, and that hydrogen transfer occurs from the ethylbenzene to ethylene. In any event, a decrease in the concentration of ethylene affords a decrease in the formation of styrene and in turn that of 1,1-DPE. The second working hypothesis that may describe the underlying chemistry is that, when the concentration of an olefin decreases, there is a selective decrease in the reaction between olefins. The product of this reaction is an oligomer, such as a dimer, which can react with an aromatic in a manner similar to that in which an undimerized olefin react with an aromatic. The products of these two reactions are two alkyl aromatics, one that corresponds to the dimer and another that corresponds to the olefin. These two alkyl aromatics can in turn react with each other to form by-product diarylalkane. Thus, applying this hypothesis to the alkylation of benzene with ethylene, the apparently anomalous formation of 1,1-DPE would result from the following reaction:

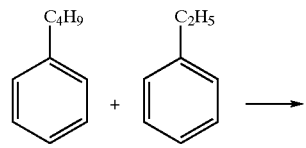

$C_4H_{10}$ + 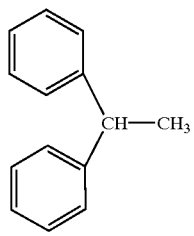

The outcome of either foregoing hypothesis and its logical consequence is that one can expect a decrease in the olefin concentration to confer benefits generally upon the alkylation of aromatics with olefins.

This invention minimizes 1,1-DPE formation and/or solid catalyst deactivation by using one or more components or portions of the reaction zone effluent stream to prevent the ethylene concentration from ever attaining the high ethylene concentrations that are present in prior art processes. It is generally known that in prior art processes the concentration of ethylene in the reaction zone decreases from a relatively high concentration at the inlet point where ethylene is introduced to a relatively low concentration at the outlet where nearly all of the ethylene has been consumed. So, even in the prior art processes, low concentrations of ethylene can occur, especially near the outlet of the reaction zone. However, it has been discovered that even the localized high ethylene concentrations that occur in prior art processes at the point of ethylene injection produce unacceptably high concentrations of 1,1-DPE and/or unacceptably rapid deactivation rates. Thus, it is now recognized that one or more components or portions of the reaction zone effluent stream can preclude localized high ethylene concentrations and minimize 1,1-DPE formation and/or solid catalyst deactivation. Moreover, it has been recognized that aliquot portions of the reaction zone effluent are preferred over other portions of the reaction zone effluent and that selective choice of an aliquot portion of the reaction zone effluent can decrease not only the deactivation rate of solid catalyst but also the formation of other undesirable by-products besides 1,1-DPE, without the requirement that the molar ratio of phenyl groups per ethyl group be decreased.

The working hypotheses explain the formation of other diarylalkanes that correspond to other olefins alkylating other aromatics. For example, in the alkylation of benzene with propylene to produce cumene, the corresponding diarylalkane would probably be 2,2-diphenylpropane (2,2-DPP). Although formation of 1,1-diphenylpropane (1,1-DPP) is also possible, 2,2-DPP formation is believed to be more probable due to preferential reaction at the secondary carbon of the propylene.

It is a broad object of this invention to improve the selectivity of and to decrease the costs of processes for the alkylation of aromatics with olefins and the transalkylation of aromatics with polyalkyl aromatics. It is a specific object of this invention to minimize the formation of 1,1-diphenylethane (1,1-DPE) and the rate of catalyst deactivation in alkylation processes that produce ethylbenzene. It is a specific object of this invention to produce an alkylation effluent stream that contains less than 1.0 wt-% diarylalkane relative to the desired monoalkyl aromatic product. It is another specific object of this invention to decrease costs associated with operating alkylation processes by decreasing the molar ratio of phenyl groups per alkyl group at alkylation conditions.

In a broad embodiment, this invention is a process for producing a monoalkyl aromatic. An aromatic feed stream comprising a feed aromatic and an olefinic feed stream comprising an olefin pass to an alkylation catalyst bed in an alkylation reaction zone. The alkylation catalyst bed contains a solid catalyst. The ratio of the weight of the olefin entering the alkylation catalyst bed in the olefinic feed stream per unit time to the sum of the weights of compounds entering the alkylation catalyst bed per the unit time, multiplied by 100, is less than 1.88. The feed aromatic is alkylated with the olefin in the alkylation catalyst bed at alkylation conditions and in the presence of the solid catalyst to form a monoalkyl aromatic. The monoalkyl aromatic has one more alkyl group corresponding to the olefin than the feed aromatic. An effluent stream comprising the monoalkyl aromatic is withdrawn from the alkylation reaction zone. The monoalkyl aromatic is recovered from the effluent stream.

Other embodiments of this invention are described in the detailed description.

INFORMATION DISCLOSURE

Prior art alkylation processes are well described in the literature.

U.S. Pat. No. 4,051,191 describes catalysts, reaction conditions, and a separation method for the recovery of cumene that uses a rectification zone and a two-column fractionation train.

U.S. Pat. Nos. 4,695,665 and 4,587,370 are particularly directed to the separation of products and the recovery of recycle streams from processes for the alkylation of aromatic hydrocarbons, and U.S. Pat. No. 4,695,665 discloses the use of a flash drum in combination with an effluent rectifier to recover unreacted feed components.

U.S. Pat. No. 4,876,408 discloses an alkylation process that uses zeolite beta having carbon deposits thereon to suppress alkylation activity and increase selectivity to monoalkylate.

U.S. Pat. No. 4,891,458 describes the use of beta zeolite for the alkylation of aromatic hydrocarbons with alkenes to produce alkyl aromatics. U.S. Pat. No. 4,891,458 also discloses that transalkylation can occur in an alkylation reactor, and that additional monoalkyl aromatic hydrocarbons can be produced in an alkylation reactor by recycling polyalkyl aromatic hydrocarbons to the alkylation reactor to undergo transalkylation. The teachings of U.S. Pat. No. 4,891,458 are incorporated herein by reference.

U.S. Pat. No. 4,922,053 describes a process for alkylating benzene with ethylene in a multibed reactor wherein polyethylbenzenes are recycled to the first alkylation bed and also to one or more of the other alkylation beds in order to increase ethylbenzene yield.

U.S. Pat. No. 5,030,786 discloses an alkylation process wherein the feed stream is dehydrated to enhance the performance of beta or Y zeolites in the alkylation process.

U.S. Pat. No. 5,227,558 discloses an alkylation process for the production of ethylbenzene that uses a steam modified zeolite beta catalyst.

U.S. Pat. No. 5,336,821 describes the use of beta zeolite for the alkylation of aromatic hydrocarbons in a process that is improved by an indirect heat exchanger to recover the heat of reaction. In one embodiment, the alkylation reactor effluent passes through the heat exchanger and is recycled to the alkylation reactor.

Prior art transalkylation processes are well described in the literature. U.S. Pat. No. 4,083,886 describes a process for the transalkylation of the alkyl aromatic hydrocarbons that uses a zeolitic catalyst. U.S. Pat. No. 4,891,458 describes the use of beta zeolite for the transalkylation of aromatic hydrocarbons with polyalkyl aromatic hydrocarbons. European Pat. Application EP 0 733 608 A1 discloses the use of an alumina silicate catalyst having an average crystal size of less than about 0.5 microns for the transalkylation of polyalkyl benzenes with benzene in a reaction zone with an alkylating agent such as ethylene.

Combination processes that produce alkyl aromatic products by using an alkylation reaction zone and a transalkylation reaction zone are also well known.

U.S. Pat. No. 4,008,290 describes a combination process in which the alkylation effluent and the transalkylation effluent are passed to a common separation zone, which separates the two effluents into product, by-product, and recycle streams including a recycle benzene stream. A portion of the alkylation effluent is recycled to the alkylation reaction zone in order to decrease the portion of the recycle benzene stream that is recycled to the alkylation reaction zone. The teachings of U.S. Pat. No. 4,008,290 are incorporated herein by reference.

U.S. Pat. No. 5,003,119 describes a combination process for producing monoalkyl aromatics in which the alkylation effluent passes to the transalkylation reaction zone, and the transalkylation effluent passes to a separation zone. U.S. Pat. No. 5,003,119 also describes passing dialkyl aromatics to the alkylation reaction zone. In addition, U.S. Pat. No. 5,003,119 teaches that diphenylalkanes are alkylation by-products and that a zeolitic catalyst can be used to convert diphenylalkanes into lighter aromatics.

U.S. Pat. No. 5,177,285 discloses an alkylation process that is improved by maintaining the feed to the alkylation zone in a relatively wet condition and the feed to the transalkylation zone in a relatively dry condition. The process operates with a relatively pure ethylene feed as an alkylating agent with a large excess of benzene.

German Pat. Application DE 19,516,717 discloses the preparation of 1,1 diphenylethanes by the addition reaction of benzene with styrene in the presence of beta zeolite.

A paper entitled "Development and Commercialization of Solid Acid Catalysts," by M. F. Bentham et al., was presented at the DGMK meeting on "Catalysis of Solid Acids and Bases" on Mar. 14–15, 1996, in Berlin, Germany, and describes the formation of diphenylethane in ethylbenzene processes by the reaction of benzene and ethylene to form styrene and ethane and by the reaction of benzene and styrene to form diphenylethane.

U.S. Pat. No. 5,902,917 describes a process for producing alkylaromatics, especially ethylbenzene and cumene, wherein a feedstock is first fed to a transalkylation zone and the entire effluent from the transalkylation zone is then cascaded directly into an alkylation zone along with an olefin alkylating agent, especially ethylene or propylene.

U.S. Pat. No. 5,998,684 describes a process for producing alkylaromatics that operates with an alkylation zone and a transalkylation zone, where the transalkylation zone and the alkylation zone are arranged for series flow and the transalkylation zone effluent is passed with an aromatic containing feed and the olefinic feed, which is preferably propylene or ethylene, to the alkylation zone.

BRIEF DESCRIPTION OF THE DRAWINGS

FIGS. 1–8 are schematic illustrations of embodiments of this invention.

DETAILED DESCRIPTION OF THE INVENTION

Figure 1:
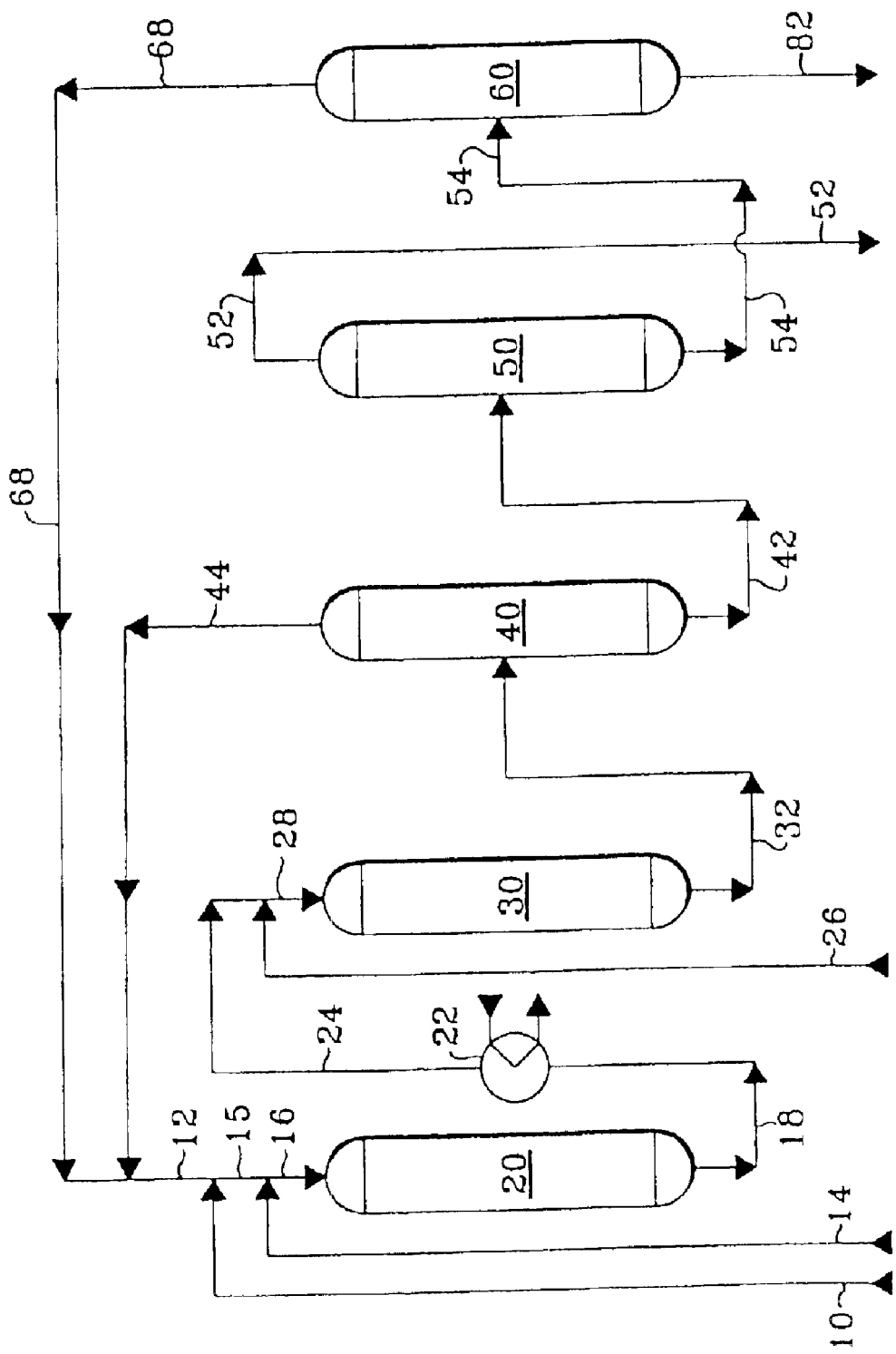

As discussed previously, this invention can be expected to be applicable generally to the alkylation of an alkylation substrate with an alkylation agent. This invention is more specifically applicable to the production of an alkyl aromatic by alkylation of a feed aromatic with an olefin. Although benzene is the principal feed aromatic of interest, feed aromatics such as alkyl-substituted benzenes, condensed ring systems generally, and alkylated derivatives thereof may be used. Examples of such feed aromatics are toluene, ethylbenzene, propylbenzene, and so forth; xylene, mesitylene, methylethylbenzene, and so on; naphthalene, anthracene, phenanthrene, methylnaphthalene, dimethylnaphthalene, and tetralin. More than one feed aromatic can be used. The feed aromatic is introduced into an alkylation reaction zone in one or more aromatic feed streams. Each aromatic feed stream may contain one or more feed aromatics. Besides the feed aromatic(s), an aromatic feed stream may contain non-aromatics, including but not limited to saturated and unsaturated cyclic hydrocarbons that have the same, one more, or one less, number of carbon atoms as the feed aromatic. For example, an aromatic feed stream containing benzene may also contain cyclohexane, cycloheptane, cyclohexenes, or cycloheptenes, as well as methylated versions of any of these hydrocarbons, or mixtures thereof. The concentration of each feed aromatic in each aromatic feed stream may range from 0.01 to 100 wt-%.

Olefins containing from 2 to 6 carbon atoms are the principal alkylating agents contemplated for this invention. Examples of such olefins include ethylene, propylene, butene-1, cis-butene-2, trans-butene-2, and isobutene. However, olefins having from 2 to 20 carbon atoms may be used effectively in this invention. More than one olefin may be used. The olefin is introduced into an alkylation reaction zone in one or more olefinic feed streams. Each olefinic feed stream may contain one or more olefins. In addition to the olefin (s), an olefinic feed stream may contain non-olefins, such as paraffins that have the same n-umber of carbon atoms as the olefin. For example, a propylene-containing olefinic feed stream may also contain propane, while an olefinic feed stream containing ethylene may also contain ethane. The concentration of each olefin in each olefinic feed stream may range from 0.01 to 100 wt-%.

The most widely practiced hydrocarbon conversion processes to which the present invention is applicable is the catalytic alkylation of benzene with ethylene to produce ethylbenzene and the catalytic alkylation of benzene with propylene to produce cumene. Although the discussion herein of the present invention will occasionally refer to a catalytic cumene reaction system, the discussion will mainly be in reference to its application to a catalytic ethylbenzene reaction system. It is not intended that this discussion limit the scope of the present invention as set forth in the claims.

In practicing some embodiments of this invention, a portion of the effluent of the alkylation reaction zone is reintroduced into the alkylation reaction zone. Unless otherwise noted in this specification, the term "portion"—when describing a process stream—refers to either an aliquot portion of the stream or a dissimilar, fraction of the stream having a different composition than the total stream from which it was derived. An aliquot portion of the stream includes a portion of the stream that has essentially the same composition as the stream from which it was derived. In some embodiments of this invention, the reintroduced portion of the alkylation reaction zone effluent may contain a transalkylation agent. Consequently, in practicing these and other embodiments of this invention a transalkylation agent may be introduced into the alkylation, reaction zone. In theory, the transalkylation agent, if present, may be any compound that is capable of transalkylating with the alkylation substrate (e.g., benzene), mixing with the alkylating agent (e.g., ethylene), and decreasing the concentration of the alkylating agent at and downstream of the alkylation agent injection point. In practice, however, the transalkylation agent preferably has a number of characteristics that are consistent with the process objective of producing high yields of high-purity product ethylbenzene. First, the transalkylation agent should increase ethylbenzene yield by transalkylation, in addition to increasing ethylbenzene yield by minimizing 1,1-DPE formation. Accordingly, a polyethylbenzene, such as diethylbenzene, triethylbenzene, and so forth up to even hexaethylbenzene, is preferred because each can transalkylate to ethylbenzene, regardless of whether each is alkylated by ethylene. Because of the possibility of alkylation of the polyethylbenzene by ethylene, however, the lighter polyethylbenzenes are more preferred over the heavier polyethylbenzenes, with diethylbenzene being most preferred.

A second characteristic of the transalkylation agent is that the transalkylation agent preferably decreases the molar ratio of phenyl groups per ethyl groups in the alkylation reaction zone. This is usually not a limiting characteristic, however, because if the transalkylation agent has at least one phenyl group and one ethyl group, then the transalkylation agent will decrease the phenyl/ethyl ratio if the ratio is greater than 1. Transalkylation agents with two or more ethyl groups per phenyl will decrease the phenyl/ethyl ratio if the ratio is greater than 0.5, and so on for transalkylation agents with more ethyl groups per phenyl group. Third, the transalkylation agent preferably should not adversely affect ethylbenzene yield. For example, toluene and cumene are not preferred, because ethylene can alkylate toluene or cumene and produce by-products that cannot be converted readily to ethylbenzene by alkylation or transalkylation. Even though generally present in the alkylation effluent, ethylbenzene is also not preferred, because ethylbenzene can shift the equilibrium of the reactions away from the formation of ethylbenzene and because ethylbenzene can react with ethylene to produce styrene and ultimately 1,1-DPE. Thus, it would be preferred to not recycle to the alkylation reaction zone a stream containing more than 75 wt-% ethylbenzene, such as the product stream produced by the ethylbenzene column of the product separation zone. Fourth, the transalkylation agent preferably should not adversely affect ethylbenzene purity. For example, xylenes are not preferred because they are relatively difficult to separate from ethylbenzene by distillation. Another reason that xylenes are not preferred is that they can adversely affect ethylbenzene yield by alkylating with ethylene.

In general, the transalkylation agent, when present, is preferably a compound that corresponds to the alkylation substrate alkylated with at least one more alkyl group corresponding to the alkylation agent than the number of alkyl groups on the desired product of alkylating the alkylation substrate with the alkylating agent. In the general case, the transalkylation agent, when present, is different from the desired product of alkylating the alkylation substrate with the alkylation agent. Where the aromatic is benzene and the olefin is ethylene, the transalkylation agent can generally be a polyalkylbenzene having two or more ethyl groups. Suitable transalkylation agents include di-, tri-, and tetra-ethyl aromatic hydrocarbons such as diethylbenzene, triethylbenzene, diethylmethylbenzene, diethylpropylbenzene, etc. Diethylbenzenes, especially ortho-, meta-, and para-diethylbenzenes, are especially preferred transalkylation agents.

In practicing this invention, the ratio of the weight of the olefin entering the alkylation catalyst bed in the olefinic feed stream per unit time to the sum of the weights of compounds entering the alkylation catalyst bed per the same unit time, multiplied by 100, is generally less than 1.88, preferably less than 1.3, and more preferably less than 0.01. This ratio is sometimes referred to herein as the olefin ratio. The alkylation conditions comprise a maximum olefin concentration based on the weight of compounds entering the alkylation catalyst bed of generally less than 1.88 wt-%, preferably less than 1.3 wt-%, and more preferably less than 0.01 wt-%.

The aromatic feed stream and the olefinic feed stream are preferably combined upstream of the alkylation catalyst bed to form a combined feed stream having preferably a homogeneous mixture and a uniform composition. If one or more other streams, besides the aromatic feed stream and the olefinic feed stream, also pass to the alkylation catalyst bed reaction zone, then preferably the other stream or streams mix with the aromatic feed stream and the olefinic feed stream so that the combined feed steam is formed from all entering streams. This helps to ensure that the olefin ratio and/or the maximum olefin concentration at alkylation conditions are minimized. The combined stream preferably also has a uniform temperature. Although the feed streams is and any other stream, if any, may combine batch-wise or on a non-continuous basis, preferably this combining occurs on a continuous basis. Given the wide range of flow rates and flowing conditions that are permissible for the feed streams and any other stream, if any, and for the alkylation zone when practicing this invention, it is not practical to describe herein all of the possible equipment and methods that can be used to combine the streams. However, persons of ordinary skill in the art of fluid mixing are capable of providing the necessary equipment and methods to bring about uniformity of concentration and intimate contact of multiple streams, even if some of the streams are of different phases, e.g., liquid phase, gas phase, mixed phase, or at supercritical conditions. Preferably, the combining occurs in either a pipeline or a vessel geometry at turbulent flow conditions. A brief introduction and references for further information on mixing of fluids can be found at pages 6–34 to 6–36 of *Perry's Chemical Engineers' Handbook*, Seventh Edition, edited by R. H. Perry, D. W. Green, and J. O. Maloney, McGraw-Hill, New York, 1997.

The alkylation reaction zone can comprise one or more alkylation catalyst beds and/or one or more alkylation catalyst reactors, and each reactor may contain one or more alkylation catalyst beds. Vessels or enclosures that can function as suitable reactors are known to persons of ordinary skill in the art of hydrocarbon processing. A common configuration of an alkylation zone employs two alkylation reactors, each of which has two alkylation catalyst beds. The number of reactors is generally less than eight, and the number of catalyst beds in a given reactor is generally less than six.

Alkylation conditions for this invention include a molar ratio of phenyl groups per alkyl group of generally from 25:1 to about 1:1. The molar ratio may be less than 1:1, and it is believed that the molar ratio may be 0.75:1 or lower. Preferably, the molar ratio of phenyl groups per ethyl group (or per propyl group, in cumene production) is below 6:1.

In general, for a given molar ratio of alkylation substrate per alkylation agent, especially an olefinic alkylation agent, the greater the molar ratio of phenyl groups to alkyl groups in the feed stream, the less is the rise in temperature in the reaction zone that occurs as a result of the alkylation reactions. The alkylation reactions have a heat of reaction of 100–150 BTU/lb-mole and are considered to be moderately exothermic. Although the reactor may have indirect heat exchange means to remove the heat as it is produced, the reactor is preferably adiabatic, and so the outlet temperature of the effluent stream is higher than the inlet temperature of the reactants. An increase in the effluent recycle ratio, as well as an increase in the molar ratio of phenyl groups to alkyl groups in the feed stream, increases the quantity of phenyl groups available to act as a heat sink in the reaction zone and thus decreases the temperature rise in the reaction zone. While in practicing this invention, the appropriate reaction temperature may be generally from 212° F. (100° C.) to the critical temperature of the alkylation substrate, which may be 887° F. (475° C.) or even higher, the inlet temperature in the reaction zone is generally from 392 to 500° F. (200 to 260° C.), and preferably from 446 to 482° F. (230 to 250° C.). Although the temperature rise that occurs in the reaction zone could be from 18 to 342° F. (10 to 190° C.) depending on the total mass flows in the reactor, the temperature rise is generally from 9 to 90° F. (5 to 50° C.), and preferably from 9 to 36° F. (5 to 20° C.).

As described previously, the temperature rise in the reaction zone may be controlled by adjusting the molar ratio of phenyl groups to ethyl groups in the feed stream. Minimizing the temperature rise helps prevent high reactor outlet temperatures, which cause undesirable side reactions such as cracking of hydrocarbons to occur. High reaction temperatures can also cause vaporization of benzene and ethylbenzene in the reaction zone. In one embodiment of this invention, the temperature rise in the reaction zone can be controlled by withdrawing an effluent stream from the reaction zone, cooling a portion of the effluent stream, and recycling the cooled portion of the effluent stream to the reaction zone. Although recycling reactor effluent to the reaction zone in this manner may be disadvantageous for some reaction zones, it is not disadvantageous for this invention because recycling reactor effluent to the reaction zone does not significantly alter the product distribution when the catalyst is zeolite beta. A significant alteration in the product distribution is a change in the concentration of any of the products in the reactor effluent stream of more than 0.5 wt-%. A significant alteration in the product distribution does not occur because at the reaction conditions zeolite beta is such an active promoter of the alkylation reaction between benzene and ethylene and of the transalkylation reaction between benzene and diethylbenzene that these reactions proceed to an extent of at least 80% and generally more than 90% of the way to equilibrium. Thus, recycling reactor effluent to the reaction zone does not interfere in a significant way with the extent of the alkylation or transalkylation reactions, and recycling reactor effluent may be employed for the purpose of controlling reaction zone temperatures.

Alkylation is preferably performed in the liquid phase. Consequently, reaction pressure needs to be sufficiently high to ensure at least a partial liquid phase. Where ethylene is the olefin, the pressure range for the reactions is usually from about 200 to about 1000 psi(g) (1379 to 6985 kPa(g)), more commonly from about 300 to about 600 psi(g) (2069 to 4137 kPa(g)), and even more commonly from about 450 to about 600 psi(g) (3103 to 4137 kPa(g)). Preferably, the reaction conditions are sufficient to maintain benzene in a liquid phase and are supercritical conditions for ethylene. Pressure is not a critical variable in the success of this invention, however, and the only criterion is that the pressure be sufficiently great to ensure at least partial liquid phase. For olefins other than ethylene, this invention may be practiced generally at a pressure of from 50 to 1000 psi(g) (345 to 6985 kPa(g)).

The weight hourly space velocity (WHSV) of ethylene may range from 0.01 to 2.0 hr$^{-1}$. As used herein, the abbreviation "WHSV" means weight hourly space velocity, which is defined as the weight flow rate per hour divided by the catalyst weight, where the weight flow rate per hour and the catalyst weight are in the same weight units. The WHSV of aromatics, including benzene and a polyalkylaromatic having at least two $C_2+$ groups, if any, is generally from 0.3 to 480 hr$^{-1}$. In a preferred embodiment, in which the polyalkyl aromatic is a diethylbenzene or a triethylbenzene, the molar ratio of benzene per ethylene is from 2:1 to 6:1, the WHSV of ethylene is from 0.1 to 1.0 hr$^{-1}$, and the WHSV of aromatics, including benzene and the polyethylbenzenes is from 0.5 to 19 hr$^{-1}$.

The principal reaction that occurs in the reaction zone are the alkylation of the benzene by ethylene to produce ethylbenzene. In addition, other reactions can occur in the reaction zone. For example, benzene can transalkylate with a polyethylbenzene to produce ethylbenzene. Also, polyethylbenzene can be alkylated with ethylene. The reactor effluent stream thus contains ethylbenzene and may also contain unreacted polyethylbenzene or a by-product of an alkylation side reaction involving the polyethylbenzene or a by-product of a transalkylation side reaction involving the polyethylbenzene. Although the extent to which other reactions form by-products is diminished by the practice of this invention, the reactor effluent stream usually contains the by-products of these side reactions. The reactor effluent stream may also contain unreacted benzene as well as a by-product of an alkylation side reaction involving benzene or a by-product of a transalkylation side reaction involving benzene. In addition, the reactor effluent stream may contain unreacted ethylene, but the concentration of unreacted ethylene is likely to be insignificant because benzene is usually present at least in a stoichiometric proportion. Although it is not common for the feed stream to contain $C_1$ to $C_3$ paraffins in addition to ethylene, if ethane is present in the feed stream then the reactor effluent stream may also contain unreacted ethane.

In practicing some embodiments of this invention, the reactor effluent stream is separated into at least two aliquot portions, in order that an aliquot portion can be recycled and passed to the alkylation reaction zone. Persons of ordinary skill in the art of fluid mechanics are capable of providing the necessary equipment and methods, including control methods, to ensure that the alkylation effluent is a uniform stream and that the portion separated from the reactor effluent and recycled to the alkylation reaction zone is an aliquot portion. For further information on distributing fluids and on controlling fluid flow, refer to pages 6–32 to 6–36 and to Section 8 of *Perry's Chemical Engineers' Handbook*, Seventh Edition.

When one aliquot portion of the alkylation effluent is recycled to and introduced into the alkylation reaction zone, at least one other aliquot portion of the alkylation effluent generally passes to a separation zone for recovering the monoalkyl aromatic. The separation zone generally comprises a benzene fractionation column in order to recycle unreacted benzene to the alkylation zone, and an ethylbenzene fractionation column in order to recover ethylbenzene as product from the heavier polyalkylbenzenes. A polyalkylbenzene fractionation column may also be used in order to separate diethylbenzenes and triethylbenzenes from the other heavier polyalkylbenzenes, particularly where the polyalkylbenzene that is present in the feed stream is a diethylbenzene or a triethylbenzene. The separation zone generally does not comprise a deethanizer unless the concentrations of unreacted ethylene, ethane, or light $C_3$-paraffins in the reactor effluent are high enough to justify their being separated from the reactor effluent stream.

Thus, in addition to producing a fraction comprising the monoalkyl aromatic, the separation zone may also produce one or more other fractions of the alkylation effluent from the aliquot portion of the alkylation effluent. Accordingly, in addition to recycling an aliquot portion of the alkylation effluent to the alkylation reaction zone, some or all of at least one of these other fractions recovered from the separation zone can also passed to the alkylation reaction zone. These other recovered fractions can comprise polyethylbenzenes, which in turn can be recycled to the alkylation reaction zone as transalkylation agents. In a commercial ethylbenzene process, several process streams produced by the separation zone can be used to supply such polyethylbenzenes to the alkylation reaction zone. Hereinafter-described FIGS. 1, 2, and 3 identify several such process streams.

The catalyst for the present invention may be any alkylation catalyst that is not deactivated rapidly as a consequence of recycling the polyalkyl aromatic to the alkylation reactor. Without limiting this invention to any particular theory, it is believed that recycling of the polyalkyl aromatic can accelerate deactivation of the catalyst in two ways: first, the polyalkyl aromatic is itself a heavy alkylated aromatic compound that deactivates the catalyst; or second, the polyalkyl aromatic is recycled in a stream that contains other compounds that are heavy alkylated aromatic compounds and that deactivate the catalyst. The catalyst for the present invention may be one of a class of aluminosilicate molecular sieves known as zeolites. The zeolitic molecular sieves suitable for use in the present invention are crystalline aluminosilicates which in the calcined form may be represented by the general formula:

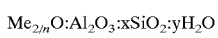

where Me is a cation, n is the valence of the cation, x has a value of from about 5 to 100, and y has a value of from about 2 to 10. Detailed descriptions of zeolites may be found in D. W. Breck, *Zeolite Molecular Sieves*, John Wiley and Sons, New York 1974, and in other standard references.

The preferred alkylation catalyst for use in this invention is a zeolitic catalyst. Without limiting this invention to any particular theory, it is believed that zeolites that have a relatively high degree of acidity and/or that exhibit a relatively high activity for catalyzing transalkylation reactions are suitable zeolites for this invention. Suitable zeolites include zeolite beta, ZSM-5, PSH-3, MCM-22, MCM-36, MCM-49, and MCM-56. Zeolite beta is described in U.S. Pat. No. 3,308,069 and Re 28,341. The topology of zeolite beta and the three zeolite beta polytypes are described in the article by Higgins, et al., in Zeolites, Vol. 8, November 1988, starting at page 446; and in the letter by M. M. J. Treacy et al., in Nature, Vol. 332, Mar. 17, 1988, starting at page 249. Suitable zeolite betas include, but are not limited to, the naturally occurring mixture of the three polytypes, any one of the three polytypes, or any combination of the three polytypes. The use of zeolite beta in alkylation and transalkylation is disclosed in U.S. Pat. Nos. 4,891,458 and 5,081,323, and the use of pristine zeolite beta in alkylation is disclosed in European Pat. EP 432,814 B1. Suitable zeolite betas include, but are not limited to, pristine zeolite beta in which the H$^+$ ion has at least partially replaced the contained metal cation, as disclosed in European Pat. EP 432,814 B1; and zeolite beta into which certain quantities of alkaline, alkaline-earth, or metallic cations have been introduced by ion exchange, as disclosed in U.S. Pat. No. 5,672,799. Various modifications of zeolite beta are also suitable for use in this invention. Suitable modified zeolite betas include, but are not limited to, zeolite beta which has been modified by steam treatment and ammonium ion treatment, as disclosed in U.S. Pat. No. 5,522,984; and zeolite beta in which the H$^+$ ion has at least partially replaced the contained metal cation, with the zeolite beta being modified by isomorphous substitution of aluminum by boron, gallium, or iron, as disclosed in European Pat. EP 432,814 B1. Suitable zeolites for use in this invention also include zeolites that are synthesized by modified preparation methods, such as, but not limited to, a preparation method comprising forming a reaction mixture comprising water, a source of silicon dioxide, a source of fluoride ions, a source of tetraethylammonium cations, and, optionally, a source of an oxide of a trivalent element, as disclosed in PCT International Publication Number WO 97/33830. ZSM-5 is described in U.S. Pat. No. 3,702,886 and Re 29,948. PSH-3 is disclosed in U.S. Pat. No. 4,439,409. MCM-22 is disclosed in U.S. Pat. Nos. 4,954,325 and 4,992,606, and its structure is described in the article in Science, Vol. 264, pp. 1910–1913 (Jun. 24, 1994). U.S. Pat. Nos. 5,077,445; 5,334, 795; and 5,600,048 describe the use of MCM-22 to produce alkylaromatics. MCM-36 is disclosed in U.S. Pat. Nos. 5,250,277 and 5,292,698. The use of a catalyst comprising MCM-36 to produce alkylaromatics such as ethylbenzene is disclosed in U.S. Pat. Nos. 5,258,565 and 5,600,048. The synthesis of MCM-49 is described in U.S. Pat. No. 5,323, 575, and the use of MCM-49 to produce alkylaromatics including the liquid phase production of ethylbenzene is described in U.S. Pat. Nos. 5,371,370; 5,493,065; and 5,600, 048. MCM-56 is disclosed in U.S. Pat. No. 5,362,697. The use of MCM-56 to produce ethylbenzene and other alkylaromatics is disclosed in U.S. Pat. Nos. 5,453,554 and 5,600,048.

It is believed that mordenite zeolite and omega zeolite can also be suitable catalysts for this,invention. Mordenite is described at pages 144–145, and omega is described at pages 128–129, of W. M. Meier and D. H. Olson, *Atlas of Zeolite Structure Types*, Third Revised Edition, Butterworth-Heinemann, Boston, 1992.

Suitable zeolites are zeolite beta as disclosed in U.S. Pat. Nos. 4,891,458 and 5,081,323, the teachings of which are incorporated herein by reference, and a steamed and ammonium exchanged zeolite beta as disclosed in U.S. Pat. No. 5,522,984, the teachings of which are incorporated herein by reference.

A preferred zeolite beta for use in alkylation in this invention is disclosed in U.S. Pat. No. 5,723,710, the teachings of which are incorporated herein by reference. This preferred zeolite is a surface-modified zeolite beta which results from acid washing of a templated native zeolite beta. That is, the formation of the surface-modified zeolite beta starts with a templated beta where the template is, for example, a tetraalkylammonium salt, such as tetraethylammonium salt. It is critical to acid wash a templated zeolite beta in order to protect the internal sites of the zeolite and to prevent dealumination. The templated zeolite beta is treated with a strong acid at a pH between about 0 up to about 2, although a pH under 1 is preferred. Acids which may be used include nitric acid, sulfuric acid, phosphoric acid, and so forth. For example, a weak, 0.01 molar nitric acid may be used in conjunction with ammonium nitrate to perform the acid wash, although substantially higher concentrations, up to about 20 weight percent nitric acid, are preferred. Nitric acid is a preferred acid since it is a non-complexing acid and therefore does not encourage dealumination. Treatment of the templated zeolite beta with strong acid may be effected over the temperature range between about 20° C. up to about 125° C. It is important that acid washing be done under conditions not so severe as to effect dealumination.

The time over which acid washing is conducted in preparing the preferred zeolite is quite temperature dependent. It is critical in the formation of the surface-modified zeolite beta that there be no significant bulk dealumination of the zeolite. Thus, as a general statement it can be said that acid washing should be done for a time insufficient to effect dealumination. For example, using 0.01 molar nitric acid and circa 40% ammonium nitrate at 70° C., contact times of 2–3 hours are found adequate to modify the environment of surface aluminum without causing significant bulk dealumination. Using circa 15% nitric acid with ammonium nitrate to treat a circa 25 weight percent slurry at 85° C., a 90-minute treatment is effective. The dependent variables in acid washing include acid concentration, slurry concentration, time and temperature, and suitable conditions at which surface-modified zeolite beta can be prepared without significant bulk dealumination are readily determined by the skilled artisan.

Next the template is removed by calcination at temperatures in the range of 550–700° C. Calcination conditions are well known in the art and need not be elaborated upon here. It also needs to be mentioned that powdered zeolite itself is not usually used as the alkylation catalyst. Therefore, in the more usual case after the templated zeolite beta is acid washed it is mixed with a conventional binder, extruded, and the extrudate is ultimately calcined. But the critical portion of the preparation of the preferred zeolite is the acid wash of the templated beta according to the foregoing description. Acid washing a calcined (i.e., non-templated) zeolite beta does not afford the surface-modified material of the preferred zeolite.

It has been found that after treatment as described above the surface aluminum atoms are chemically modified. It has been hypothesized that the modification is in the form of replacement of strong acid sites at the catalyst surface by weaker acid sites. What has been definitely observed is that the surface aluminums of the preferred modified zeolite beta have 2p binding energies as measured by x-ray photoelectron spectroscopy of at least 74.8 electron volts.

In another embodiment, this invention is a method for controlling a process for the production of a monoalkyl aromatic. In this control method, the production of diarylalkane relative to that of a monoalkyl aromatic is controlled by adjusting the olefin ratio and/or the maximum olefin concentration of an alkylation catalyst bed in the alkylation reaction zone. In the case of ethylbenzene production, for example, the effluent stream of the alkylation reaction zone is analyzed for ethylbenzene and for diphenylethane and/or alkylated diphenylalkanes using conventional gas chromatography. If the concentration of diphenylalkanes relative to that of ethylbenzene in the effluent is greater than desired, then the olefin ratio to the alkylation catalyst bed may be decreased, or the maximum olefin concentration at alkylation conditions may be decreased by, for instance, recycling a larger weight of alkylation effluent to the alkylation catalyst bed. If the concentration of diphenylalkanes relative to that of ethylbenzene in the effluent is less than desired, then the olefin ratio to the alkylation catalyst bed, or the maximum olefin concentration at alkylation conditions, may be increased recycling a lower weight of alkylation effluent or by increasing the weight of olefin passing to the bed.

FIGS. 1–8 illustrate embodiments of the invention. For clarity and simplicity, some items associated with the operation of the process have not been shown. These items include flow and pressure control valves, pumps, heat exchangers, temperature and pressure monitoring systems, reactor and fractionator internals, etc., which may be of customary design. Such representation of these embodiments is not intended to limit the scope of the present invention as set forth in the claims.

Figure 2:
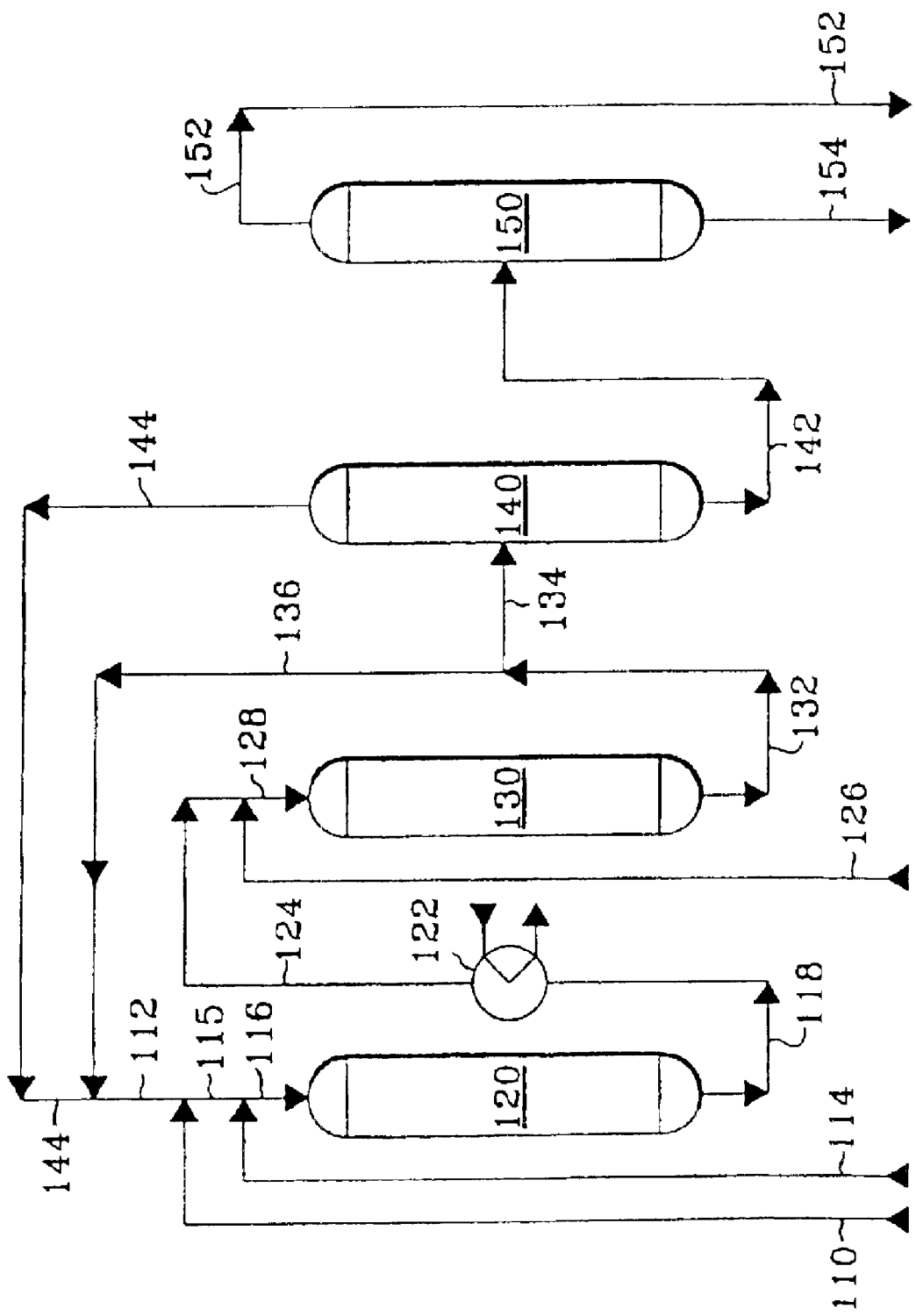

In the description of FIGS. 1–3 that follows, the reactors in FIGS. 1–3 are referred to as alkylation-transalkylation reactors in order to indicate that not only alkylation reactions but also transalkylation reactions occur in the reactors. It is believed that the occurrence of transalkylation reactions in the reactors is not a requirement of the present invention. This invention is a process that operates at a low ratio or a low concentration of olefins, whether or not transalkylation reactions occur in the reactors. Of course, depending on the conditions and catalyst in the reactors and on the compounds that enter the alkylation reactors, transalkylation reactions may occur in the reactors, and the occurrence of those reactions may be preferred in some embodiments.

Referring now to FIG. 1, FIG. 1 illustrates a preferred embodiment of this invention in which a polyethylbenzene column overhead stream is recycled to the alkylation-transalkylation reactor. The overhead stream of the polyethylbenzene column typically contains only diethylbenzenes and triethylbenzenes. One advantage of this embodiment is that the overhead stream of the polyethylbenzene column contains a relatively low concentration of ethylbenzene, which is not a polyethylbenzene and cannot, therefore, transalkylate with benzene to produce ethylbenzene. Another advantage of this embodiment is that the polyethylbenzene column overhead stream does not contain the heaviest polyethylbenzenes that are produced in the alkylation-transalkylation reactors because the polyethylbenzene column is operated so as to reject the heaviest polyethylbenzenes in the polyethylbenzene column bottom stream. The absence of the heaviest polyethylbenzenes from the stream that is recycled to the alkylation-transalkylation reactors reduces the deactivation rate of the alkylation-transalkylation catalyst because the heavy polyethylbenzenes tend to foul the active sites of the catalyst.

In FIG. 1, a stream comprising ethylene enters the process in a line 14 and is admixed with a stream flowing through a line 15 that comprises benzene, diethylbenzenes, and triethylbenzenes, thereby producing a first alkylation-transalkylation reactor feed stream carried by a line 16. The benzene that is present in the stream flowing through the line 15 is benzene that has been added as make-up to the process and benzene that has been recycled within the process. Make-up benzene can enter the process in a line 10, admix with a stream flowing through a line 12, and flow into the line 15. Recycle benzene can flow from a benzene column 40, flow through a line 44, admix with a recycled polyethylbenzene column overhead stream flowing in a line 68, flow through the line 12, and flow into the line 15. The recycle polyalkylbenzenes flowing in the line 15 comprise diethylbenzenes and triethylbenzenes from the polyethylbenzene column overhead stream. Thus, the first alkylation-transalkylation reactor feed stream flowing through the line 16 contains ethylene, benzene, diethylbenzenes, and triethylbenzenes. The first reactor feed stream flowing through line 16 may be heated in a heat exchanger or a heater, which is not shown, and enters a first alkylation-transalkylation reactor 20. The first reactor feed stream contacts a zeolite beta catalyst maintained at reaction conditions to form ethylbenzene by alkylating benzene with at least a portion of the ethylene and by transalkylating benzene with at least a portion of the diethylbenzenes or triethylbenzenes. The first alkylation-transalkylation reactor effluent stream comprises benzene, ethylbenzene, by-products of the alkylation of benzene with ethylene, and by-products of the alkylation and transalkylation of diethylbenzenes and triethylbenzenes in the first reactor feed stream. Typically, the by-products in the first reactor effluent stream comprise diethylbenzenes, triethylbenzenes, butylbenzenes, dibutylbenzenes, tributylbenzenes, ethylbutylbenzenes, diethylbutylbenzenes, and diphenylethane. The first reactor effluent stream exits the first reactor 20 in a line 18.

The first alkylation-transalkylation reactor effluent stream enters a heat exchanger 22, where the first reactor effluent stream is cooled by exchanging heat indirectly with boiler feed water to produce low pressure steam. The cooled first reactor effluent stream passes through a line 24 and is admixed with ethylene that enters the process in a line 26. This produces a second alkylation-transalkylation reactor feed stream carried by a line 28. The second alkylation-transalkylation reactor feed stream may be heated in a heat exchanger or a heater, which is not shown, and enters a second alkylation-transalkylation reactor 30. The second reactor feed stream contacts a zeolite beta catalyst to alkylate benzene with ethylene and to transalkylate benzene with diethylbenzenes and triethylbenzenes in order to produce ethylbenzene. The second alkylation-transalkylation reactor effluent stream can include not only by-products of the alkylation of benzene with ethylene and of the transalkylation of benzene with diethylbenzenes and triethylbenzenes but also by-products of the alkylation and transalkylation of components of the first alkylation-transalkylation reactor effluent stream because the first alkylation-transalkylation reactor effluent stream is passed to the second alkylation-transalkylation reactor 30. Typically, the by-products in the second reactor effluent stream comprise those by-products listed previously as being in the first reactor effluent stream. The second reactor effluent stream exits the second alkylation-transalkylation reactor 30 in a line 32. The second alkylation-transalkylation reactor effluent stream may be depressured by passing through a pressure control valve which is not shown, may be heated in a heater or heat exchanger which is also not shown, or both. The second alkylation-transalkylation reactor effluent then enters a benzene column 40.

The benzene column 40 separates the second alkylation-transalkylation reactor effluent stream by distillation into two streams. A benzene column overhead stream comprising benzene exits the benzene column through the line 44 and is recycled to the first alkylation-transalkylation reactor 20 as described previously. A benzene column bottom stream comprising the product ethylbenzene and the by-products including polyethylbenzenes exits the benzene column in a line 42 and enters an ethylbenzene column 50.

The ethylbenzene column 50 separates the benzene column bottom stream by distillation into two streams. An ethylbenzene column overhead stream comprising the product ethylbenzene exits the ethylbenzene column 50 in a line 52 and is recovered from the process. An ethylbenzene column bottom stream comprises by-product ethylbenzenes, typically including diethylbenzenes, triethylbenzenes, butylbenzenes, dibutylbenzenes, tributylbenzenes, ethylbutylbenzenes, diethylbutylbenzenes, and diphenylethane. The ethylbenzene column bottom stream exits the ethylbenzene column 50 in a line 54, and passes to a polyethylbenzene column 60.

The polyethylbenzene column 60 separates the ethylbenzene column bottom stream into two streams. A polyethylbenzene column bottom stream comprising polyethylbenzenes heavier than triethylbenzene exits from the bottom of the polyethylbenzene column 60 in a line 82 and is rejected from the process. The polyethylbenzene column overhead stream comprising diethylbenzenes and triethylbenzenes exits the polyethylbenzene column 60 in the line 68 and recycles to the first alkylation-transalkylation reactor 20 as described previously.

FIG. 2 illustrates another embodiment of this invention in which the second alkylation-transalkylation reactor effluent stream rather than the polyethylbenzene column overhead stream is recycled to the first alkylation-transalkylation reactor. One of the advantages of this embodiment in which a portion of the second alkylation-transalkylation reactor effluent stream is recycled is because at least in theory the second alkylation-transalkylation reactor effluent stream can be recycled at a rate that is limited only by economic considerations. Except for the portion of the second alkylation-transalkylation reactor effluent stream that is passed downstream to product separation facilities, the second alkylation-transalkylation reactor effluent stream is available for recycle in what amounts to an unlimited quantity. Just as importantly, and unlike other streams in the process, the second alkylation-transalkylation reactor effluent stream can be recycled to the alkylation-transalkylation reactors without interfering with the extent to which the alkylation and transalkylation reactions proceed.

Referring now to FIG. 2, make-up ethylene enters the process in a line 114 and combines with a stream flowing through a line 115 that is formed from make-up benzene from a line 110, recycle benzene from a benzene column 140 via lines 144 and 112, and a recycled portion of the second alkylation-transalkylation reactor effluent stream via lines 136 and 112. Thus, the stream flowing through the line 115 carries at least one recycle polyalkylbenzene comprising at least two $C_2$ groups, such as diethylbenzenes, triethylbenzenes, and heavier polyalkylbenzenes. Whether any or all of these recycle polyalkylbenzenes is in fact present in the stream in line 115 depends on which of these recycle polyalkylbenzenes is present in the portion of the second alkylation-transalkylation reactor effluent stream that is recycled through the line 136. Accordingly, in this embodiment the first alkylation-transalkylation reactor feed stream flowing through the line 116 contains ethylene, benzene, and components of the second alkylation-transalkylation reactor effluent stream, including polyethylbenzenes. Polyethylbenzenes in the second alkylation-transalkylation reactor effluent stream can include not only by-products of the alkylation of benzene with ethylene but also by-products of the alkylation and transalkylation of various components of the second alkylation-transalkylation reactor effluent stream because the second alkylation-transalkylation reactor effluent stream is itself recycled to the first alkylation-transalkylation reactor 120. The first alkylation-transalkylation reactor feed stream flows through a line 116 and enters first alkylation-transalkylation reactor 120. The first alkylation-transalkylation reactor effluent stream exits the first alkylation-transalkylation reactor 120 in a line 118, is cooled in a heat exchanger 122, passes through a line 124, and combines with make-up ethylene from a line 126 to produce the second alkylation-transalkylation reactor feed stream. The second alkylation-transalkylation reactor feed stream enters a second alkylation-transalkylation reactor 130 through a line 128. The second alkylation-transalkylation reactor effluent stream exits the second alkylation-transalkylation reactor 130 in a line 132. A portion of the second alkylation-transalkylation reactor effluent stream is cooled in a heat exchanger or a cooler, which is not shown, and is recycled to the first alkylation-transalkylation reactor 120 through the lines 136, 112, 115, and 116. Another portion of the second alkylation-transalkylation reactor effluent stream passes through a line 134. This other portion of the second alkylation-transalkylation reactor effluent stream may be depressured, heated, or both, and then enters a benzene column 140.

The benzene column 140 separates the second reactor effluent stream into a benzene column overhead stream comprising benzene that is is recycled to the first alkylation-transalkylation reactor 120 via the line 144 as described previously and into a benzene column bottom stream comprising ethylbenzene and by-product alkylbenzenes that flows through a line 142 to an ethylbenzene column 150. The ethylbenzene column 150 separates the benzene column bottom stream into an ethylbenzene column overhead stream comprising ethylbenzene that is recovered from the process through a line 152 and into an ethylbenzene column bottom stream comprising by-product alkylbenzenes such, as diethylbenzenes, triethylbenzenes, butylbenzenes, dibutylbenzenes, tributylbenzenes, ethylbutylbenzenes, diethylbutyl-benzenes, and diphenylethane. The ethylbenzene column bottom stream flows through a line 154 and is rejected from the process.

FIG. 3 illustrates another embodiment of this invention in which the ethylbenzene column bottom stream, rather than the second reactor effluent stream or the polyethylbenzene column overhead stream, is recycled to the first reactor. One of the advantages of this embodiment is that the bottom stream of the ethylbenzene column contains a relatively low concentration of ethylbenzene, which is not a polyalkylbenzene and cannot transalkylate with benzene to produce ethylbenzene. In addition, the absence of ethylbenzene from the stream that is recycled to the first alkylation-transalkylation reactor promotes the formation of ethylbenzene in the reactors because of the equilibrium between benzene, polyethylbenzenes, and ethylbenzene. On the other hand, in comparison with the polyethylbenzene column overhead stream, the ethylbenzene column bottoms stream contains a relatively high concentration of polyalkylbenzenes, which tend to increase the deactivation rate of the alkylation-transalkylation catalyst.

Referring now to FIG. 3, make-up ethylene enters the process in a line 214 and combines with a stream flowing through a line 215 that is formed from make-up benzene from a line 210, a recycled portion of a benzene column overhead stream via lines 244 and 212, and a recycled portion of the ethylbenzene column bottom stream via lines 254, 258, and 212. Thus, the feed stream in line 216 to first alkylation-transalkylation reactor 220 contains ethylene, benzene, and components that are present in the ethylbenzene column bottom stream such as diethylbenzenes, triethylbenzenes, butylbenzenes, dibutylbenzenes, tributylbenzenes, ethylbutyl-benzenes, diethylbutyl-benzenes, and diphenylethane. The first alkylation-transalkylation reactor effluent stream exits the first alkylation-transalkylation reactor 220 in a line 218, is cooled in a heat exchanger 222, passes through a line 224, and combines with make-up ethylene from a line 226 to produce the second alkylation-transalkylation reactor feed stream. The second alkylation-transalkylation reactor feed stream enters a second alkylation-transalkylation reactor 230 through a line 228. The second alkylation-transalkylation reactor effluent stream exits the second alkylation-transalkylation reactor 230 via a line 232 and enters a benzene column 240. The benzene column 240 produces the benzene column overhead stream comprising benzene in the line 244 which is recycled to the first alkylation-transalkylation reactor 220 as described previously and a benzene column bottom stream comprising the product ethylbenzene and by-product alkylbenzenes that flows through a line 242 to an ethylbenzene column 250. An ethylbenzene column overhead stream comprising ethylbenzene is recovered from the process through a line 252. An ethylbenzene column bottom stream comprising by-product alkylbenzenes such as diethylbenzenes, triethylbenzenes, butylbenzenes, dibutylbenzenes, tributylbenzenes, ethylbutylbenzenes, diethylbutylbenzenes, and diphenylethane flows through a line 254. A portion of the ethylbenzene column bottom stream is recycled via the line 258 to the first alkylation-transalkylation reactor 220 as described previously. A small part of the ethylbenzene column bottoms stream is removed from the process via a line 256 in order to provide a purge for heavy polyalkylbenzenes.

Other embodiments of this invention include combinations of the is three just-described embodiments. For example, instead of only one stream, two or three streams can be recycled to the first alkylation-transalkylation reactor. Thus, for example, in FIG. 1, a portion of the effluent stream of the second alkylation-transalkylation reactor 30 or a portion of the bottoms stream of the ethylbenzene column 50, or both, can be recycled to the first alkylation-transalkylation reactor 20.

In the description of FIGS. 4–8 that follows, the reactors in FIGS. 4–8 are referred to as alkylation reactors, except for reactor 630 in FIG. 6, which is referred to as a transalkylation reactor. Although alkylation reactions take place in the alkylation reactors in FIGS. 4–8, it should be noted that transalkylation reactions may also take place in the alkylation reactors in FIGS. 4–8, depending on the conditions and catalyst in the reactors. Referring to reactors in FIGS. 4–8 as alkylation reactors is not intended to exclude transalkylation reactions from occurring in such alkylation reactors.

Referring now to FIG. 4, a stream comprising ethylene enters the process in line 404 and is admixed with a stream flowing through line 402 that comprises benzene and with a cooled aliquot portion of alkylation reactor effluent flowing through line 422, thereby producing an alkylation reactor feed stream flowing through the line 406 that contains ethylene, benzene, and components of the alkylation reactor effluent. The turbulence that occurs as a result of the combining and admixing of the streams and the flowing of the alkylation reactor feed stream through line 406 makes the concentration of olefin (ethylene) uniform in the alkylation reactor feed stream. The alkylation reactor feed stream flowing through line 406 may be heated in a heat exchanger or heater, which is not shown, and enters alkylation reactor 410. Turbulence within the heat exchanger or heater, if present, may further help to ensure uniform ethylene concentration. The alkylation reactor feed stream contacts bed 412 of solid alkylation catalyst comprising zeolite beta or MCM-22 maintained at reaction conditions to form ethylbenzene by alkylating benzene with at least a portion of the ethylene. The reactor effluent stream exits reactor 410 via line 414, and then divides into two aliquot portions. One aliquot portion passes through line 416 to another alkylation reactor or a product separation zone, which is not shown. The other aliquot portion of the reactor effluent stream flows through line 418, enters heat exchanger 420, where the aliquot portion is cooled by exchanging heat indirectly with boiler feed water to produce low pressure steam, and then flows through line 422 to combine with the streams flowing in lines 402 and 404, as described previously.

Referring now to FIG. 5, ethylene enters via line 524 and combines with a stream flowing through a line 526 to form the stream flowing through line 528. The stream in line 526 is formed from benzene in line 576 and an aliquot portion of the recycled and cooled aliquot portion of the second alkylation reactor effluent stream in line 566. Thus, the stream flowing through line 528, which is the first alkylation reactor feed stream, contains ethylene, benzene, and recycled components of the second alkylation reactor effluent stream, which may include recycled polyethylbenzenes such as diethylbenzenes, triethylbenzenes, and heavier polyethylbenzenes. Turbulent flow and in-line mixers, which are not shown, in line 528 help ensure good mixing and uniformity of the ethylene concentration in the feed stream as it enters first alkylation reactor 530. The first alkylation reactor 530 contains two beds of solid alkylation catalyst, 532 and 534, and the first alkylation reactor feed stream enters bed 532. An effluent stream exits bed 532 and combines with an ethylene-containing stream flowing through line 536 to form the feed stream for bed 534. The introduction of ethylene between beds 532 and 534 is done in a manner and/or using distribution devices so that the concentration of the ethylene concentration in the feed stream for bed 534 is substantially uniform. An effluent stream exits bed 534 and first alkylation reactor 530 via line 538, is cooled in heat exchanger 540, passes through line 542, and combines with ethylene from line 544 to produce the stream flowing through line 546. The second alkylation reactor feed stream flowing in line 547 is formed by combining the stream flowing in line 546 with a recycled and cooled aliquot portion of the second alkylation reactor effluent stream in line 545. Turbulence in lines 546 and 547 helps ensure that the ethylene concentration is uniform in the second alkylation reactor feed stream as the stream enters second alkylation reactor 550. The second alkylation reactor 550 contains two beds of solid alkylation catalyst, 553 and 555, and the second alkylation reactor feed stream enters bed 553. An effluent stream exits bed 553 and combines with an ethylene-containing stream flowing through line 548 to form the feed stream for bed 555. The introduction of ethylene between beds 553 and 555 is done in a manner so that the concentration of the ethylene in the feed stream to bed 555 is uniform. An effluent stream exits bed 555 and leaves alkylation reactor 550 via line 552. The effluent stream in line 552 divides into two aliquot portions. One aliquot portion flows through line 554 to a downstream alkylation reactor or to a product separation zone, which is not shown. The other aliquot portion of the second alkylation reactor effluent stream flows through line 558, enters heat exchanger 560 where the aliquot portion is cooled, flows through line 562, and then itself divides into two aliquot portions. One aliquot flows to the first alkylation reactor 530 via line 566 and the other aliquot portion flows to the second alkylation reactor 550 via line 545, as described previously.

Referring now to FIG. 6, a stream comprising polyethylbenzenes, such as diethylbenzenes and triethylbenzenes, enters the process via line 624 and is admixed with a stream flowing through line 676 that comprises benzene thereby producing a transalkylation reactor feed stream flowing through line 628. The transalkylation reactor feed stream in line 628 may be heated in a heat exchanger or heater, which is not shown, and enters transalkylation reactor 630, where the feed stream contacts bed 632 of solid transalkylation catalyst comprising a solid alkylation catalyst maintained at reaction conditions to form ethylbenzene by transalkylating benzene with at least a portion of the polyethylbenzenes. However, it should be noted that, regarding this embodiment of the invention, it is believed that it is not critical that the transalkylation reaction zone be any particular transalkylation zone. Rather, it is believed instead that the transalkylation zone may be any suitable transalkylation zone, such as those described in U.S. Pat. Nos. 4,008,290; 4,774,377; and 4,891,458. The transalkylation reactor effluent stream exits bed 632 and transalkylation reactor 630 via line 638 and passes through heat exchanger 640, where the transalkylation reactor effluent stream may be cooled or heated, depending on the temperature of the transalkylation reactor effluent stream relative to the desired temperature in the alkylation reactor 650. After exiting heat exchanger 640, the transalkylation reactor effluent stream flows through line 642 and combines with ethylene from line 644 to produce the stream flowing through line 646. The alkylation reactor feed stream flowing in line 647 is formed by combining the stream flowing in line 646 with a recycled and cooled aliquot portion of the alkylation reactor effluent stream in line 662. Turbulence in lines 646 and 647 helps ensure that the ethylene concentration is uniform in the alkylation reactor feed stream as the stream enters alkylation reactor 650. The alkylation reactor 650 contains two beds of solid alkylation catalyst, 653 and 655, and the alkylation reactor feed stream enters bed 653. An effluent stream exits bed 653 and combines with an ethylene-containing stream flowing through line 648 to form the feed stream for bed 655. The introduction of ethylene between beds 653 and 655 is done in a manner so that the concentration of the ethylene in the feed stream to bed 655 is uniform. An effluent stream exits bed 655 and leaves alkylation reactor 650 via line 652. The alkylation reactor effluent stream in line 652 divides into two aliquot portions. One aliquot portion flows through line 654 to a downstream alkylation reactor or to a product separation zone, which is not shown. The other aliquot portion of the alkylation reactor effluent stream flows through line 658, enters heat exchanger 660 where the aliquot portion is cooled, flows through line 662, and then combines with the stream flowing through line 646, as described previously.

Figure 7:
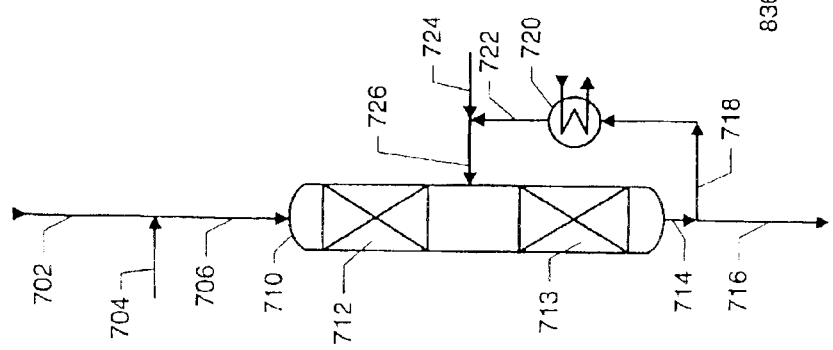

Referring now to FIG. 7, ethylene enters via line 704 and combines with a benzene-containing stream flowing through line 702 to form the stream flowing through line 706. Turbulent flow in line 706 helps ensure good mixing and uniformity of the ethylene concentration in the feed stream as it enters alkylation reactor 710. The alkylation reactor 710 contains two beds of solid alkylation catalyst, 712 and 713, and the alkylation reactor feed stream enters bed 712. In bed 712, ethylene alkylates benzene to produce ethylbenzene, but it should be noted that, regarding this embodiment of the invention, it is believed that it is not critical that bed 712 be any particular alkylation catalyst bed. Rather, it is believed instead that the alkylation that occurs in bed 712 may done in any suitable alkylation zone, even in an alkylation zone which is not in the same alkylation reactor as bed 713. Suitable alkylation zones include as those described in U.S. Pat. Nos. 4,008,290; 4,774,377; and 4,891,458. An effluent stream exits bed 712 and combines with a stream flowing through line 726 to form the feed stream for bed 713. The stream in line 726 is formed by combining an ethylene-containing stream in line 724 with a cooled aliquot portion of alkylation reactor effluent flowing through line 722. Turbulent flow in line 726 helps ensure good mixing and uniformity of the ethylene concentration in the stream in line 726 as it enters alkylation reactor 710. The introduction of the stream in line 726 between beds 712 and 713 is done in a manner so that the concentration of the ethylene in the feed stream to bed 713 is uniform. An effluent stream exits bed 713 and alkylation reactor 710 via line 714, and then divides into two aliquot portions. One aliquot portion passes through line 716 to another alkylation reactor or a product separation zone, which is not shown. The other aliquot portion of the reactor effluent stream flows through line 718, is cooled in heat exchanger 720, and then flows through line 722 to combine with the ethylene-containing stream in line 724, as described previously.

Figure 8:
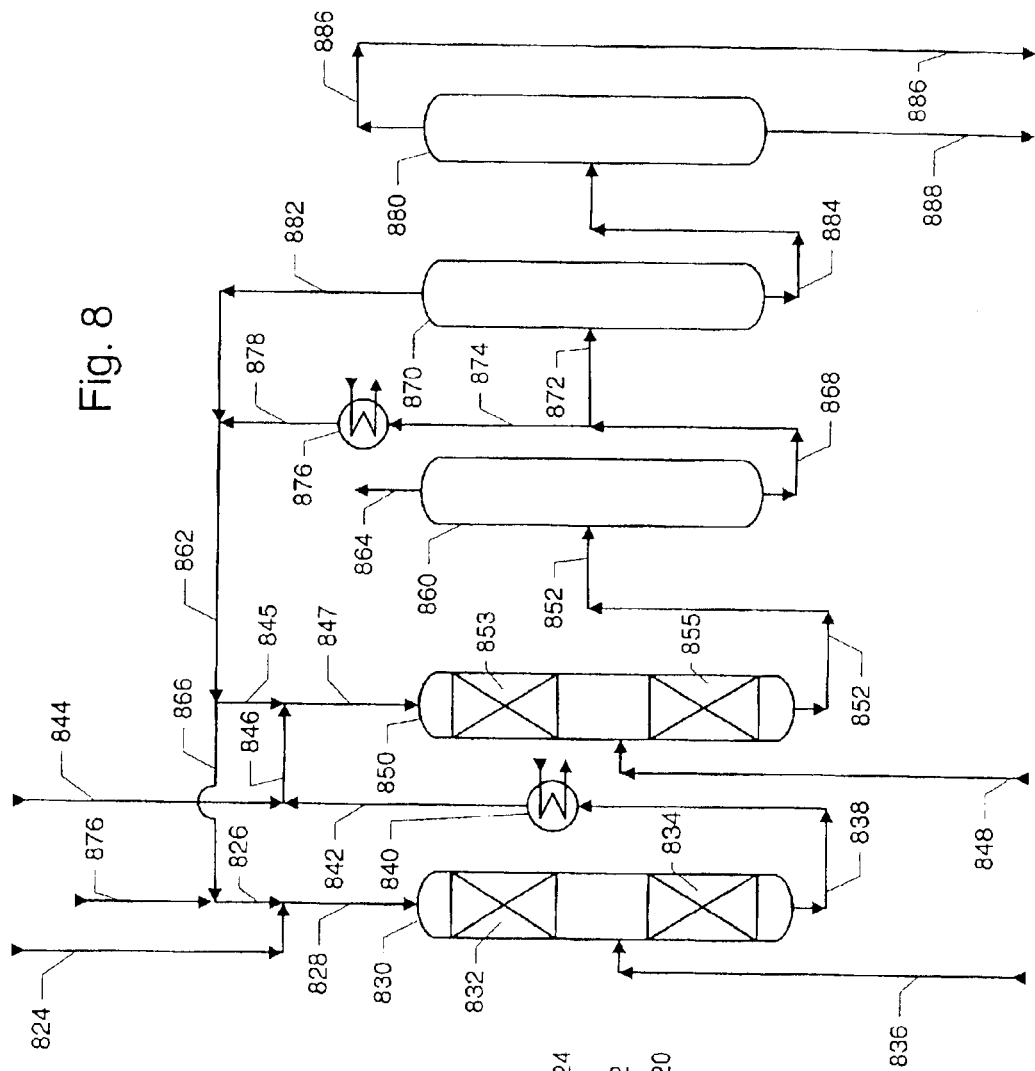

Referring now to FIG. 8, ethylene enters via line 824 and combines with a stream flowing through line 826 to form the stream flowing through line 828. The stream in line 826 is formed by combining benzene from line 876 and the stream flowing in line 866, which is an aliquot portion of the stream flowing in line 862 and which contains components from the bottoms stream of deethanizer column 860 and the overhead stream of benzene column 870. The stream flowing through line 828, which is the first alkylation reactor feed stream, contains ethylene, benzene, and recycled components, which may include recycled polyethylbenzenes such as diethylbenzenes, triethylbenzenes, and heavier polyethylbenzenes. Turbulent flow helps ensure good mixing and uniformity of the ethylene concentration in the feed stream as it enters first alkylation reactor 830. The first alkylation reactor 830 contains two beds of solid alkylation catalyst, 832 and 834, and the first alkylation reactor feed stream enters bed 832. An effluent stream exits bed 832 and combines with an ethylene-containing stream flowing through line 836 to form the feed stream for bed 834. The introduction of ethylene between beds 832 and 834 is done in a manner so that the concentration of the ethylene in the feed stream for bed 834 is uniform. An effluent stream exits bed 834 and first alkylation reactor 830 via line 838, is cooled in heat exchanger 840, passes through line 842, and combines with ethylene from line 844 to produce the stream flowing through line 846. The second alkylation reactor feed stream flowing in line 847 is formed by combining the stream flowing in line 846 with the stream flowing in line 845, which is an aliquot portion of the recycle stream flowing through line 862. Turbulence in lines 846 and 847 helps ensure that the ethylene concentration is uniform in the second alkylation reactor feed stream as the stream enters second alkylation reactor 850. The second alkylation reactor 850 contains two beds of solid alkylation catalyst, 853 and 855, and the second alkylation reactor feed stream enters bed 853. An effluent stream exits bed 853 and combines with an ethylene-containing stream flowing through line 848 to form the feed stream for bed 855. The introduction of ethylene between beds 853 and 855 is done in a manner so that the concentration of the ethylene in the feed stream to bed 855 is uniform. An effluent stream exits bed 855 and leaves alkylation reactor 850 via line 852.

The effluent stream in line 852 enters deethanizer column 860, which separates lighter hydrocarbons such as ethane and compounds lighter than ethane from the entering stream in line 852. The separated components are recovered in an overhead stream in line 864 and routed to downstream processing, which is not shown. The bottom stream of deethanizer 860 flows through line 868 and divides into two aliquot portions. One aliquot portion flows through line 874 to heat exchanger 876. Heat exchanger 876 cools the aliquot portion to a temperature that is suitable for recycling to alkylation reactors 830 and 850 in the manner shown in FIG. 8. It should be pointed out that, in some variations of the embodiment shown in FIG. 8, heat exchanger 876 may not be required, due to the cooling effect that may accompany flashing of the stream in line 852 in conjunction with the deethanizing step. In any event, the stream in line 878 combines with the overhead stream in line 882 from benzene column 870, and the combined stream flows through line 862. The other aliquot portion of the deethanizer bottom stream in line 868 flows through line 872 to benzene column 870. The benzene column 870 separates the aliquot portion of the deethanizer bottom stream by distillation into two streams. The benzene column overhead stream comprising benzene exits the benzene column 870 through line 882 and combines with the stream flowing in line 878 for recycling, as described previously. A benzene column bottom stream comprising the product ethylbenzene and the by-products including polyethylbenzenes exits the benzene column in line 884 and enters ethylbenzene column 880. Ethylbenzene column 880 separates the benzene column bottom stream by distillation into two streams. An ethylbenzene column overhead stream comprising the product ethylbenzene exits the ethylbenzene column 880 in line 886 and is recovered from the process. An ethylbenzene column bottom stream comprising by-product ethylbenzenes and diphenylethanes exits the ethylbenzene column 880 in line 888 and is sent to further processing facilities, such as to a polyethylbenzene column, which is not shown in FIG. 8.

EXAMPLES

Catalyst A is Fresh Alkylation Catalyst Comprising Zeolite Beta

A sample of Catalyst A was used to produce ethylbenzene by alkylating benzene with ethylene at alkylation conditions at which heavy alkylaromatics were occluded on the surface and within the internal pore space of the sample of Catalyst A. After having been used for alkylation, the sample of Catalyst A had a content of occluded heavy alkylaromatics of about 5% by weight of the catalyst weight. While being contacted with air, the sample of Catalyst A having occluded heavy alkylaromatics was heated from ambient temperature to 1202° F. (650° C.) over a period of three hours, was maintained at 1202° F. (650° C.) for three hours, and then was cooled to room temperature. The sample of Catalyst A after cooling is referred to in these Examples as Catalyst B.

Catalyst C is a fresh alkylation catalyst comprising zeolite beta.

Catalyst D is a fresh alkylation catalyst comprising 80 wt-% 'ultrastabilized' zeolite Y and 20 wt-% alumina binder.

Catalysts E, F, and G are fresh alkylation catalysts comprising 70 wt-% zeolite beta and 30 wt-% alumina binder.

The zeolite beta for Catalyst E was prepared in substantially the same manner as described in U.S. Pat. No. 5,522,984. The zeolite betas for Catalysts F and G was prepared in substantially the same manner as described in U.S. Pat. No. 5,723,710.

Catalyst H is a fresh alkylation catalyst comprising 70 wt-% MCM-22 and 30 wt-% alumina binder.

In the Examples 1–9 that follow, the net reactor effluent stream is the total reactor effluent stream less the portion, if any, of the total reactor effluent stream that is recycled to the reactor. Efficiency is defined with respect to ethylene and is computed by subtracting the weight of ethylene in the net reactor effluent stream from the weight of ethylene in the make-up ethylene to the reactor, divided by the weight of ethylene in the net reactor effluent stream, times 100. Selectivity of 1,1-DPE is defined as the concentration in weight percent of 1,1-DPE in the net reactor effluent stream, computed on the basis of the net reactor effluent stream being free of benzene and light compounds. In general, the yield of a compound is defined as the product of conversion and selectivity of that compound, divided by 100. However, the ethylbenzene yield has a special definition in that it is defined as the sum of the individual yields of ethylbenzene, diethylbenzene, and triethylbenzene. This computation of the ethylbenzene yield accounts for the total yield of ethylbenzene that would be produced if all the diethylbenzene and triethylbenzene in the product stream was transalkylated to ethylbenzene in a transalkylation zone and subsequently recovered.

In addition, in the Examples the benzene liquid hourly space velocity (LHSV) is computed using only the make-up benzene and does not include the benzene in the portion, if any, of the total reactor effluent stream that is recycled to the catalyst bed. As used herein, the abbreviation "LHSV" means liquid hourly space velocity, which is defined as the volumetric flow rate of liquid per hour divided by the catalyst volume, where the liquid volume and the catalyst volume are in the same volumetric units. Also, because the molar ratio of phenyl groups per ethyl group (or per propyl group) is essentially the same in the total reactor feed stream and the total reactor effluent stream, the molar ratio of phenyl groups per ethyl group (or per propyl group) is not significantly affected by recycling any portion of the total reactor effluent stream.

In Examples 1–7, the catalyst is contacted with a combined feed stream containing fresh benzene, fresh ethylene, a recycled aliquot portion of the reactor effluent stream (in Examples 1, 3, 5, 6, and 7 only), and fresh diethylbenzene (in Example 6 only). Where a portion of the reactor effluent stream is recycled to the reactor, the ratio of the weight of the recycled portion of the reactor effluent stream per the weight of fresh benzene and fresh ethylene was 2.0.

TABLE 1

Effect of Ethylene Concentration on 1,1-DPE Formation at Various Molar Ratios of Phenyl Groups per Ethyl Group using Zeolite Beta Catalysts

| | Example | | | | | | |
|---|---|---|---|---|---|---|---|
| | 1 | 2 | 3 | 4 | 5 | 6 | 7 |
| Catalyst | B | B | B | B | B | A | A |
| Phenyl/Ethyl, mol/mol | 5.21 | 5.25 | 4.09 | 4.27 | 1.81 | 4.54 | 4.55 |
| Maximum temp., ° C. | 241.9 | 252.5 | 201.7 | 252.1 | 231.8 | 242 | 242 |

TABLE 1-continued

Effect of Ethylene Concentration on 1,1-DPE Formation at Various Molar Ratios of Phenyl Groups per Ethyl Group using Zeolite Beta Catalysts

| | Example | | | | | | |
|---|---|---|---|---|---|---|---|
| | 1 | 2 | 3 | 4 | 5 | 6 | 7 |
| Temp. rise, ° C. | 15.9 | 33.3 | 20.9 | 34.7 | 24.1 | 23.4 | 25.5 |
| Pressure, psi (g) | 550 | 550 | 550 | 550 | 550 | 550 | 550 |
| Benzene LHSV, hr$^{-1}$ | 3.9 | 4.1 | 2.6 | 3.3 | 1.3 | 3.9 | 2.9 |
| Recycle effluent/fresh feed, wt/wt | 2.0 | 0 | 2.0 | 0 | 2.0 | 2.0 | 2.0 |
| Ethylene concentration in combined feed wt-% | 2.15 | 6.4 | 2.79 | 7.75 | 5.52 | 1.88 | 2.44 |
| EB yield, wt-% | 99.82 | 99.79 | 99.83 | 99.73 | 98.24 | 99.49 | 99.38 |
| 1,1-DPE selectivity, wppm | 886 | 928 | 895 | 1230 | 11180 | 2900 | 3100 |
| 1,1-DPE/EB in reactor effluent (wt-%/wt-%) ×10$^2$ | .101 | .105 | .105 | .143 | 1.74 | .357 | .348 |
| Ethylene efficiency, wt-% | 99.9 | 99.9 | 99.9 | 99.9 | 99.5 | 99.8 | 99.8 |

A comparison of Examples 1 and 2 shows the effect of recycling a portion of the reactor effluent stream to the reactor in order to decrease the concentration of ethylene in the feed stream at nearly the same molar ratio of phenyl groups per ethyl group (5.21 and 5.25). Recycling a portion of the effluent stream in Example 1 increases the ethylbenzene yield, decreases the 1,1-DPE selectivity, and decreases the ratio of 1,1-DPE per ethylbenzene in the effluent stream.

A comparison of Examples 3 and 4 shows the effect of recycling a portion of the reactor effluent stream to the reactor in order to decrease the concentration of ethylene in the feed stream at molar ratios of phenyl groups per ethyl group (4.09 and 4.27) that are lower than in Examples 1 and 2. Recycling a portion of the reactor effluent stream in Example 3 increases the ethylbenzene yield, decreases the 1,1-DPE selectivity, and decreases the ratio of 1,1-DPE per ethylbenzene in the effluent stream, even though the molar ratio of phenyl groups per ethyl group is lower in Example 3 than in Example 4.

Example 5 shows the effect of recycling a portion of the reactor effluent stream to the reactor at a lower molar ratio of phenyl groups per ethyl group than in Examples 1 through 4, but without decreasing the concentration of ethylene in the feed stream. With the concentration of ethylene in the feed stream being relatively high at 5.52 wt-%, then even though the molar ratio of phenyl groups per ethyl group is 1.81:1, the ethylbenzene yield is lower, the 1,1-DPE selectivity is higher, and the ratio of 1,1-DPE per ethylbenzene in the effluent stream is higher than in Examples 1 through 4.

In Example 6, fresh diethylbenzene was passed to the reactor in order to simulate the effect of recycling diethylbenzene. Fresh diethylbenzene constituted 4.5 wt-% of the weight of the fresh benzene, fresh ethylene, and fresh diethylbenzene that was passed to the reactor. The molar ratio of phenyl groups per ethyl group of 4.54 takes into account the phenyl and ethyl groups of the fresh diethylbenzene. A comparison of Examples 6 and 7 shows the effect of introducing diethylbenzene to the reactor while recycling a portion of the effluent stream to the reactor at nearly the same molar ratios of phenyl groups per ethyl group. Introducing diethylbenzene increases the ethylbenzene yield and decreases the 1,1-DPE selectivity.

In Examples 8 and 9, the catalyst is contacted with a combined feed stream containing fresh benzene, fresh propylene, and a recycled aliquot portion of the reactor effluent stream. The ratio of the weight of the recycled portion of the reactor effluent stream per the weight of fresh benzene and fresh propylene was 1.5 in Example 8 and 1.75 in Example 9. The position of the maximum temperature (due to the exothermic reaction) in the catalyst bed was noted. Deactivation was determined by noting the position of the maximum temperature after a suitable interval of time (e.g., 48 hours) at test conditions. Deactivation is calculated by taking the difference in these two positions (in inches), dividing by the bed length (in inches), and then dividing by the time interval (in days). The results are multiplied by 100% to give a deactivation rate in percent of catalyst bed/day.

TABLE 2

Effect of Recycling Reactor Effluent on Catalyst Deactivation Rate at the Same Phenyl/Propyl Ratio using Zeolite Beta Catalyst

| Example | 8 | 9 |
|---|---|---|
| Catalyst | C | C |
| Phenyl/Propyl, mol/mol | 4 | 4 |
| Maximum temp., ° C. | 180 | 180 |
| Temp. rise ° C. | 25 | 23 |
| Pressure, psi(g) | 500 | 500 |
| Benzene LHSV, hr$^{-1}$ | 4 | 4 |
| Recycle effluent/fresh feed, wt/wt | 1.5 | 1.75 |
| Propylene concentration in combined feed, wt-% | 4.7 | 4.3 |
| Deactivation rate, %/day | 3.45 | 2.86 |

A comparison of Examples 8 and 9 shows that increasing the recycle ratio of the effluent stream to the catalyst bed at the same molar ratio of phenyl groups per propyl group decreases the rate of catalyst deactivation. Although these data showing a decrease in the deactivation rate were obtained while Catalyst C was used to alkylate benzene with propylene, it is believed that a similar decrease in the rate of catalyst deactivation would be observed if Catalyst C is used to alkylate benzene with ethylene.

In Examples 10 and 11, the catalyst is contacted with a combined stream comprising fresh benzene, fresh ethylene, and a recycled aliquot portion of the reactor effluent stream (in Example 10 only). In Example 10, the ratio of the weight of the recycled portion of the reactor effluent stream per the weight of fresh benzene was 3. Deactivation rates were determined by the calculation, method described previously for Examples 8 and 9.

TABLE 3

Effect of Recycling Reactor Effluent on 1,1-DPE Formation and on Catalyst Deactivation Rate at the Same Phenyl/Ethyl Ratio Using Zeolite Y Catalyst

| Example | 10 | 11 |
|---|---|---|
| Catalyst | D | D |
| Phenyl/Ethyl, mol/mol | 5.0 | 5.0 |
| Maximum temp., °C. | 240 | 240 |
| Pressure, psi(g) | 550 | 550 |
| Ethylene LHSV, hr$^{-1}$ | 0.3 | 0.3 |
| Recycle effluent/fresh benzene, wt/wt | 3 | 0 |
| 1,1-DPE/EB in reactor effluent, (wt-%/wt-%) × 10$^2$ | 2.76 | 2.45 |
| Deactivation rate, %/day | 2.5 | 1.7 |

A comparison of Examples 10 and 11 shows that increasing the recycle ratio of the effluent stream to the catalyst bed at the same molar ratio of phenyl groups per ethyl group increases the ratio of 1,1-DPE per ethylbenzene in the effluent stream and increases the rate of catalyst deactivation. Thus, in contrast to zeolite beta, zeolite Y's performance worsens as a result of recycling reactor effluent.

Examples 12 and 13 are illustrative of a preferred catalyst for use in this invention.

Example 12

Preparation of acid washed zeolite betas. To a solution of 1428 grams ammonium nitrate in 3224 grams distilled water was added 932 grams of 70 weight percent nitric acid and the mixture was heated to 85° C. A dry weight of 1416 grams of commercial zeolite beta, SiO$_2$ 92.2 wt-%, Al$_2$O$_3$ 7.0 wt-%, LOI 24.3 wt-%, and N$_2$ BET 672 m$^2$/g, was added and this mixture was stirred at 85° C. for 90 minutes. The slurry was filtered and washed using 10 liters of distilled water and then dried at 100° C. for 16 hours. After drying, the material was calcined at 650° C. for 3 hours in air. Analyses of this sample showed 91.7 wt-% SiO$_2$, 6.1 wt-% Al$_1$O$_3$, and a molar ratio SiO$_2$/Al$_2$O$_3$ of 25.5. The sample was examined by x-ray photoelectron spectroscopy (XPS) to determine binding energies, as well as the surface silicon: aluminum atomic ratio. The results are summarized in Table 4.

TABLE 4

| Peak: | Binding Energies (eV): |
|---|---|
| Al2p | 75.20 |
| Si2p | 103.30 |
| O 1s | 532.43 |
| | Surface Concentrations (atomic %): |
| Al | 1.93 |
| Si | 29.91 |
| Si/Al (bulk) | 13 |
| Si/Al (XPS) | 16 |

Example 13

Alkylation of benzene with propylene. The sample described in Example 12 was bound with alumina (70/30 zeolite/binder), extruded (1/16" extrudates), dried, and then calcined at 650° C. for 2 hours. 10 cc of 1/16" extrudates were loaded into a reactor to form a bed ½" in diameter and 3¾" to 4" long. The catalyst was activated for 12 hours by passing a stream of benzene over the catalyst at 140° C., 500 psig, and 6 benzene LHSV. Temperature was adjusted to the desired run temperature and the feed switched to a blend of 6 weight percent propylene in benzene at 6 LHSV. The position of the maximum temperature (due to the exothermic reaction) in the bed was noted. The deactivation rate was determined by the calculation method described previously for Examples 8 and 9. The catalyst was tested at 130° C., and the deactivation rate was 10.3% per day.

Example 14

A feed stream was prepared containing benzene and ethylene and having a molar ratio of benzene per ethylene of about 6:1. For this feed stream, the molar ratio of phenyl groups per ethyl groups is equal to the molar ratio of benzene per ethylene. The feed stream was contacted with zeolite beta in a reactor at a temperature of 252° C. (486° F.), at a weight hourly space velocity of 7.5 hr$^{-1}$, and at a pressure of 565 psia that was sufficient to maintain the benzene and the ethylene in the liquid phase. A first portion of the effluent stream from the reactor was cooled, recycled, and combined with the feed stream at a weight ratio of effluent recycle to feed stream of 2:1. A second portion of the effluent stream, which was recovered as product from the reactor, contained about 18 wt-% ethylbenzene and about 1.5 wt-% diethylbenzene.

Example 15

An aromatic stream was prepared containing 95.5 wt-% benzene and 4.5 wt-% para-diethylbenzene. A feed stream was prepared by admixing the aromatic stream with ethylene to attain a molar ratio of phenyl groups per ethyl groups of about 4.5:1. For this feed stream, the molar ratio of phenyl groups per ethyl groups is less than the molar ratio of benzene per ethylene, because of the presence of para-diethylbenzene. The feed stream was contacted with zeolite beta in a reactor at a temperature of 252° C. (486° F.), at a weight hourly space velocity of 7.5 hr$^{-1}$, and at a pressure of 565 psia that was sufficient to maintain the benzene and the ethylene in the liquid phase. A first portion of the effluent stream from the reactor was cooled, recycled, and combined with the feed stream at a weight ratio of effluent recycle to feed stream of 2:1. A second portion of the effluent stream, which was recovered as product from the reactor, contained about 21 wt-% ethylbenzene and about 3.5 wt-% diethylbenzene. The molar ratio of meta-diethylbenzene per para-diethylbenzene in the product was about 2.2:1.

A comparison of Examples 14 and 15 shows that in Example 15 a significant quantity of diethylbenzene converted to ethylbenzene by transalkylation. If no diethylbenzene had transalkylated, the product in Example 15 would have contained about 6.0 wt-% diethylbenzene, which is the sum of the 1.5 wt-% diethylbenzene in the product of Example 14 plus the 4.5 wt-% diethylbenzene in the feed stream of Example 15. In fact, the product in Example 15 contained about 3.5 wt-% diethylbenzene. The difference between 6.0 wt-% and 3.5 wt-% is attributable to transalkylation of diethylbenzene in Example 15.

In addition, Example 15 also shows that the para-diethylbenzene in the feed isomerized to meta-diethylbenzene almost to the extent that would be predicted by equilibrium at the conditions of Example 15. Therefore, these results indicate that the conclusion that transalkylation occurred at the conditions of Example 15 applies not only to the case where the feed stream contains para-diethylbenzene, but would also apply to the case where the feed stream contains meta-diethylbenzene or ortho-diethylbenzene. This is because even if the feed stream had contained meta-diethylbenzene or ortho-diethylbenzene instead of para-diethylbenzene, these other isomers would have isomerized to para-diethylbenzene and the experimental results would have been the same.

Example 16

Example 15 was repeated, except that the reaction temperature was 242° C. (468° F.) instead of 252° C. (486° F.). The product contained about 4.2 wt-% diethylbenzene instead of about 3.5 wt-% diethylbenzene.

A comparison of Examples 15 and 16 shows that a decrease in temperature decreases the quantity of diethylbenzene converted to ethylbenzene by transalkylation. Because increasing the weight ratio of effluent recycle to feed stream with all other variables constant tends to decrease the reaction temperature, Example 16 indicates that an increase in weight ratio of effluent recycle to feed stream would decrease the quantity of diethylbenzene converted to ethylbenzene by transalkylation. Likewise, a decrease in weight ratio of effluent recycle to feed stream would increase the quantity of diethylbenzene converted to ethylbenzene by transalkylation. Of course, the change in reaction temperature that occurs as a result of the change in weight ratio of effluent recycle to feed stream could be compensated for by a change in the amount of heat added or removed from the reactor.

Examples 17–23

In each of Examples 17–23, the catalyst is-contacted with a combined stream comprising fresh benzene, fresh olefin, and a recycled aliquot portion of the reactor effluent stream. The ratio of the weight of the recycled portion of the reactor effluent stream per the weight of fresh benzene and fresh olefin ranged from 5.0 to 18.0. Deactivation rates were determined by the calculation method described previously for Examples 8 and 9.

TABLE 5

Effect of Recycling Reactor Effluent on Catalyst Deactivation Rate

| | Example | | | | | | | |
|---|---|---|---|---|---|---|---|---|
| | 17 | 18 | 19 | 20 | 21 | 22 | 23 | 24 |
| Catalyst | E | E | F | F | G | G | H | H |
| Olefin: propylene ($C_3$) or ethylene ($C_2$) | $C_3$ | $C_3$ | $C_2$ | $C_2$ | $C_3$ | $C_3$ | $C_3$ | $C_3$ |
| Phenyl/Alkyl ratio, mol/mol | 3.8 | 1.9 | 3.8 | 1.0 | 1.0 | 1.0 | 2.1 | 2.1 |
| Maximum temperature, ° C. | 150 | 160 | 180 | 200 | 173 | 182 | 92 | 131 |
| Temperature rise, ° C. | 16 | 16 | 14 | 16 | 20 | 29 | 27 | 13 |
| Pressure, psi (g) | 500 | 500 | 550 | 550 | 500 | 500 | 500 | 500 |
| Benzene LHSV, $hr^{-1}$ | 4.0 | 2.0 | 2.0 | 0.5 | 0.6 | 0.8 | 1.8 | 0.9 |
| Recycle effluent/fresh feed, wt/wt | 5.2 | 10.1 | 10.4 | 18.0 | 17.5 | 11.3 | 5.8 | 14.1 |
| Olefin concentration in combined feed, wt-% | 2.0 | 2.0 | 1.3 | 1.4 | 1.9 | 2.8 | 3.1 | 1.4 |
| Deactivation rate, %/day | 2.3 | 1.1 | 2.1 | 1.3 | 2.0 | 4.5 | 3.1 | 0.9 |

Examples 17–24 show that increasing the recycle ratio of the effluent stream to the catalyst bed decreases the rate of catalyst deactivation. Comparisons of Examples 17 and 18 (for propylene) and of Examples 19 and 20 (for ethylene) show that this benefit occurs even when the olefin concentration is the same, and comparisons of Examples 21 and 22 (with Catalyst G) and of Examples 23 and 24 (with Catalyst H) show that this benefit occurs when the molar ratio of phenyl groups per alkyl (propyl) group is constant. Example 21 shows that a higher recycle ratio decreases the rate of catalyst deactivation, despite the fact that the maximum temperature is lower than that of Example 22.

What is claimed is:

1. A method for controlling a process for producing a monoalkyl aromatic, said method comprising:
  a) passing an aromatic feed stream comprising a feed aromatic and an olefinic feed stream comprising an olefin to an alkylation catalyst bed in an alkylation reaction zone, wherein said alkylation catalyst bed contains a solid crystal line catalyst and wherein the ratio of the weight of said olefin entering said alkylation catalyst bed in said olefinic feed stream per unit time to the sum of the weight; of compounds entering said alkylation catalyst bed per said unit time, multiplied by 100, is less than 1.88, wherein said solid crystalline catalyst comprises a zeolite selected from the group consisting of zeolite beta, ZSM-5, PSH-3, MCM-22, MCM-36, MCM-49, MCM-56, mordenite, and omega;
  b) alkylating said feed aromatic with said olefin in said alkylation catalyst bed at alkylation conditions and in the presence of said solid crystalline catalyst to form a monoalkyl aromatic, wherein said monoalkyl aromatic has one more alkyl group corresponding to said olefin than said feed aromatic;
  c) withdrawing an effluent stream from said alkylation reaction zone, wherein said effluent stream comprises said monoalkyl aromatic and has a content of diarylalkane of less than 1.0 wt-% diarylalkane relative to said monoalkyl aromatic;
  d) measuring said content of diarylalkane in said effluent stream;
  e) adjusting the ratio of the weight of olefin entering the process to the sum of the weights of compounds entering the process based on said content of diarylalkane; and
  f) recovering said monoalkyl aromatic from said effluent stream.

2. The method of claim 1 characterized in that a first aliquot portion of said effluent stream is recycled to said alkylation catalyst bed and said monoalkyl aromatic is recovered from a second aliquot portion of said effluent stream.

3. The method of claim 1 further characterized in that said effluent stream comprises a dilution compound selected from the group consisting of a paraffin, the feed aromatic, a dialkyl aromatic having two more alkyl group corresponding to said olefin than said feed aromatic, and a trialkyl aromatic having three more alkyl group corresponding to said olefin than said feed aromatic, and at least a portion of said dilution compound is recycled to said alkylation catalyst bed.

4. The method of claim 1 further characterized in that a dilution stream comprising an aromatic is passed to said alkylation catalyst bed.

5. The method of claim 1 wherein said ratio is less than 0.01.

6. The process of claim 1 further characterized in that said monoalkyl aromatic is selected from the group consisting of ethylbenzene and cumene.

7. A method for controlling a process for producing a monoalkyl aromatic, said method comprising measuring the content of diarylalkane in the effluent of the process and adjusting the maximum olefin concentration in the process based on said content.

8. The method of claim 7 further characterized in that said maximum olefin concentration is less than 1.88.

9. The method of claim 7 further characterized in that said maximum olefin concentration is less than 0.01.

10. The method of claim 7 further characterized in that said effluent contains less than 1.0 wt-% diarylalkane relative to said monoalkyl aromatic.

11. A method for controlling a process for producing a monoalkyl aromatic, said method comprising:
  a) passing an aromatic feed stream comprising a feed aromatic and an olefinic feed stream comprising an olefin to an alkylation catalyst bed in an alkylation reaction zone;
  b) alkylating said feed aromatic with said olefin in said alkylation catalyst bed at alkylation conditions and in the presence of a solid crystalline catalyst to form a monoalkyl aromatic, wherein said monoalkyl aromatic has one more alkyl group corresponding to said olefin than said feed aromatic, and wherein said alkylation conditions comprise a maximum olefin concentration based on the weight of compounds entering said alkylation catalyst bed of less than 1.88 wt-%, wherein said solid crystalline catalyst comprises a zeolite selected from the group consisting of zeolite beta, ZSM-5, PSH-3, MCM-22, MCM-36, MCM-49, MCM- 56, mordenite, and omega;
  c) withdrawing an effluent stream from said alkylation reaction zone, wherein said effluent stream comprises said monoalkyl aromatic and has a content of diarylalkane of less than 1.0 wt-% diarylalkane relative to said monoalkyl aromatic;
  d) measuring said content of diarylalkane in said effluent stream;
  a) adjusting said maximum olefin concentration based on said content of diarylalkane; and
  f) recovering said monoalkyl aromatic from said effluent stream.

12. The method of claim 11 further characterized in that said maximum olefin concentration is less than 0.01 wt-%.

13. The method of claim 11 further characterized in that a first aliquot portion of said effluent stream is recycled to said alkylation catalyst bed and said monoalkyl aromatic is recovered from a second aliquot portion of said effluent stream.

14. The method of claim 11 further characterized in that a dilution stream comprising an aromatic is passed to said alkylation catalyst bed.

* * * * *

UNITED STATES PATENT AND TRADEMARK OFFICE
CERTIFICATE OF CORRECTION

PATENT NO. : 6,872,864 B2
DATED : March 29, 2005
INVENTOR(S) : Gregory J. Gajda et al.

It is certified that error appears in the above-identified patent and that said Letters Patent is hereby corrected as shown below:

Column 32,
Line 11, "crystal line" should be replaced with -- crystalline --.
Line 14, "weight;" should be replaced with -- weights --.
Line 17, "zeclite" should be replaced with -- zeolite --.

Signed and Sealed this

Seventh Day of June, 2005

JON W. DUDAS
*Director of the United States Patent and Trademark Office*